United States Patent
Haddock et al.

(10) Patent No.: US 12,403,313 B2
(45) Date of Patent: Sep. 2, 2025

(54) METHODS AND SYSTEMS FOR ESTIMATING NEURAL ACTIVATION BY STIMULATION USING A STIMULATION SYSTEM

(71) Applicant: Boston Scientific Neuromodulation Corporation, Valencia, CA (US)

(72) Inventors: Andrew James Haddock, Los Angeles, CA (US); Tianhe Zhang, Studio City, CA (US); Mahsa Malekmohammadi, Sherman Oaks, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 558 days.

(21) Appl. No.: 17/838,778

(22) Filed: Jun. 13, 2022

(65) Prior Publication Data
US 2022/0395690 A1    Dec. 15, 2022

Related U.S. Application Data

(60) Provisional application No. 63/210,799, filed on Jun. 15, 2021.

(51) Int. Cl.
| | |
|---|---|
| A61N 1/36 | (2006.01) |
| A61B 5/00 | (2006.01) |
| A61B 5/374 | (2021.01) |

(52) U.S. Cl.
CPC .......... *A61N 1/36128* (2013.01); *A61B 5/374* (2021.01); *A61B 5/7246* (2013.01); *A61B 5/748* (2013.01)

(58) Field of Classification Search
None
See application file for complete search history.

(56) References Cited

U.S. PATENT DOCUMENTS

| | | |
|---|---|---|
| 3,999,555 A | 12/1976 | Person |
| 4,144,889 A | 3/1979 | Tyers et al. |
| 4,177,818 A | 12/1979 | De Pedro |
| 4,341,221 A | 7/1982 | Testerman |
| 4,378,797 A | 4/1983 | Osterholm |

(Continued)

FOREIGN PATENT DOCUMENTS

| | | |
|---|---|---|
| EP | 813889 | 12/1997 |
| EP | 1048320 | 11/2000 |

(Continued)

OTHER PUBLICATIONS

Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.

(Continued)

*Primary Examiner* — Shirley X Jian
(74) *Attorney, Agent, or Firm* — Branch Partners PLLC; Bruce E. Black

(57) ABSTRACT

A method for estimating neural activation arising from stimulation by a stimulation system includes identifying different neural elements stimulated by the stimulation; obtaining a neural response signal resulting from the stimulation by the stimulation system; and decomposing the neural response signal to estimate neural activation of each of the different neural elements.

20 Claims, 10 Drawing Sheets

(56) References Cited

U.S. PATENT DOCUMENTS

| | | |
|---|---|---|
| 4,445,500 A | 5/1984 | Osterholm |
| 4,735,208 A | 4/1988 | Wyler et al. |
| 4,765,341 A | 8/1988 | Mower et al. |
| 4,841,973 A | 6/1989 | Stecker |
| 5,067,495 A | 11/1991 | Brehm |
| 5,099,846 A | 3/1992 | Hardy |
| 5,222,494 A | 6/1993 | Baker, Jr. |
| 5,255,693 A | 10/1993 | Dutcher |
| 5,259,387 A | 11/1993 | dePinto |
| 5,304,206 A | 4/1994 | Baker, Jr. et al. |
| 5,344,438 A | 9/1994 | Testerman et al. |
| 5,361,763 A | 11/1994 | Kao et al. |
| 5,452,407 A | 9/1995 | Crook |
| 5,560,360 A | 10/1996 | Filler et al. |
| 5,565,949 A | 10/1996 | Kasha, Jr. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,651,767 A | 7/1997 | Schulmann |
| 5,711,316 A | 1/1998 | Elsberry et al. |
| 5,713,922 A | 2/1998 | King |
| 5,716,377 A | 2/1998 | Rise et al. |
| 5,724,985 A | 3/1998 | Snell et al. |
| 5,749,904 A | 5/1998 | Gliner et al. |
| 5,749,905 A | 5/1998 | Gliner et al. |
| 5,776,170 A | 7/1998 | MacDonald et al. |
| 5,782,762 A | 7/1998 | Vining |
| 5,843,148 A | 12/1998 | Gijsbers et al. |
| 5,859,922 A | 1/1999 | Hoffmann |
| 5,868,740 A | 2/1999 | LeVeen et al. |
| 5,897,583 A | 4/1999 | Meyer et al. |
| 5,910,804 A | 6/1999 | Fortenbery et al. |
| 5,925,070 A | 7/1999 | King et al. |
| 5,938,688 A | 8/1999 | Schiff |
| 5,938,690 A | 8/1999 | Law et al. |
| 5,978,713 A | 11/1999 | Prutchi et al. |
| 6,016,449 A | 1/2000 | Fischell et al. |
| 6,029,090 A | 2/2000 | Herbst |
| 6,029,091 A | 2/2000 | de la Rama et al. |
| 6,050,992 A | 4/2000 | Nichols |
| 6,058,331 A | 5/2000 | King |
| 6,066,163 A | 5/2000 | John |
| 6,080,187 A | 6/2000 | Alt et al. |
| 6,083,162 A | 7/2000 | Vining |
| 6,094,598 A | 7/2000 | Elsberry et al. |
| 6,096,756 A | 8/2000 | Crain et al. |
| 6,106,460 A | 8/2000 | Panescu et al. |
| 6,109,269 A | 8/2000 | Rise et al. |
| 6,128,538 A | 10/2000 | Fischell et al. |
| 6,129,685 A | 10/2000 | Howard, III |
| 6,146,390 A | 11/2000 | Heilbrun et al. |
| 6,161,044 A | 12/2000 | Silverstone |
| 6,167,311 A | 12/2000 | Rezai |
| 6,181,969 B1 | 1/2001 | Gord |
| 6,192,266 B1 | 2/2001 | Dupree et al. |
| 6,205,361 B1 | 3/2001 | Kuzma |
| 6,208,881 B1 | 3/2001 | Champeau |
| 6,240,308 B1 | 5/2001 | Hardy et al. |
| 6,246,912 B1 | 6/2001 | Sluijter et al. |
| 6,253,109 B1 | 6/2001 | Gielen |
| 6,289,239 B1 | 9/2001 | Panescu et al. |
| 6,301,492 B1 | 10/2001 | Zonenshayn |
| 6,310,619 B1 | 10/2001 | Rice |
| 6,319,241 B1 | 11/2001 | King |
| 6,336,899 B1 | 1/2002 | Yamazaki |
| 6,343,226 B1 | 1/2002 | Sunde et al. |
| 6,351,675 B1 | 2/2002 | Tholen et al. |
| 6,353,762 B1 | 3/2002 | Baudino et al. |
| 6,366,813 B1 | 4/2002 | Dilorenzo |
| 6,368,331 B1 | 4/2002 | Front et al. |
| 6,389,311 B1 | 5/2002 | Whayne et al. |
| 6,393,325 B1 | 5/2002 | Mann et al. |
| 6,421,566 B1 | 7/2002 | Holsheimer |
| 6,435,878 B1 | 8/2002 | Reynolds et al. |
| 6,442,432 B2 | 8/2002 | Lee |
| 6,463,328 B1 | 10/2002 | John |
| 6,491,699 B1 | 12/2002 | Henderson et al. |
| 6,494,831 B1 | 12/2002 | Koritzinsky |
| 6,507,759 B1 | 1/2003 | Prutchi et al. |
| 6,510,347 B2 | 1/2003 | Borkan |
| 6,516,227 B1 | 2/2003 | Meadows et al. |
| 6,517,480 B1 | 2/2003 | Krass |
| 6,539,263 B1 | 3/2003 | Schiff |
| 6,560,490 B2 | 5/2003 | Grill et al. |
| 6,579,280 B1 | 6/2003 | Kovach et al. |
| 6,600,956 B2 | 7/2003 | Maschino et al. |
| 6,606,523 B1 | 8/2003 | Jenkins |
| 6,609,029 B1 | 8/2003 | Mann et al. |
| 6,609,031 B1 | 8/2003 | Law et al. |
| 6,609,032 B1 | 8/2003 | Woods et al. |
| 6,622,048 B1 | 9/2003 | Mann et al. |
| 6,631,297 B1 | 10/2003 | Mo |
| 6,654,642 B2 | 11/2003 | North et al. |
| 6,662,053 B2 | 12/2003 | Borkan |
| 6,675,046 B2 | 1/2004 | Holsheimer |
| 6,684,106 B2 | 1/2004 | Herbst |
| 6,687,392 B1 | 2/2004 | Touzawa et al. |
| 6,690,972 B2 | 2/2004 | Conley et al. |
| 6,690,974 B2 | 2/2004 | Archer et al. |
| 6,692,315 B1 | 2/2004 | Soumillion et al. |
| 6,694,162 B2 | 2/2004 | Hartlep |
| 6,694,163 B1 | 2/2004 | Vining |
| 6,708,096 B1 | 3/2004 | Frei et al. |
| 6,741,892 B1 | 5/2004 | Meadows et al. |
| 6,748,098 B1 | 6/2004 | Rosenfeld |
| 6,748,276 B1 | 6/2004 | Daignault, Jr. et al. |
| 6,778,846 B1 | 8/2004 | Martinez et al. |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,845,267 B2 | 1/2005 | Harrison et al. |
| 6,850,802 B2 | 2/2005 | Holsheimer |
| 6,895,280 B2 | 5/2005 | Meadows et al. |
| 6,909,913 B2 | 6/2005 | Vining |
| 6,937,891 B2 | 8/2005 | Leinders et al. |
| 6,937,903 B2 | 8/2005 | Schuler et al. |
| 6,944,497 B2 | 9/2005 | Stypulkowski |
| 6,944,501 B1 | 9/2005 | Pless |
| 6,950,707 B2 | 9/2005 | Whitehurst |
| 6,969,388 B2 | 11/2005 | Goldman et al. |
| 6,993,384 B2 | 1/2006 | Bradley et al. |
| 7,003,349 B1 | 2/2006 | Andersson et al. |
| 7,003,352 B1 | 2/2006 | Whitehurst |
| 7,008,370 B2 | 3/2006 | Tanner et al. |
| 7,008,413 B2 | 3/2006 | Kovach et al. |
| 7,035,690 B2 | 4/2006 | Goetz |
| 7,043,293 B1 | 5/2006 | Baura |
| 7,047,082 B1 | 5/2006 | Schrom et al. |
| 7,047,084 B2 | 5/2006 | Erickson et al. |
| 7,050,857 B2 | 5/2006 | Samuelsson et al. |
| 7,054,692 B1 | 5/2006 | Whitehurst et al. |
| 7,058,446 B2 | 6/2006 | Schuler et al. |
| 7,082,333 B1 | 7/2006 | Bauhahn et al. |
| 7,107,102 B2 | 9/2006 | Daignault et al. |
| 7,126,000 B2 | 10/2006 | Ogawa et al. |
| 7,127,297 B2 | 10/2006 | Law et al. |
| 7,136,518 B2 | 11/2006 | Griffin et al. |
| 7,136,695 B2 | 11/2006 | Pless et al. |
| 7,142,923 B2 | 11/2006 | North et al. |
| 7,146,219 B2 | 12/2006 | Sieracki et al. |
| 7,146,223 B1 | 12/2006 | King |
| 7,151,961 B1 | 12/2006 | Whitehurst |
| 7,155,279 B2 | 12/2006 | Whitehurst |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,191,014 B2 | 3/2007 | Kobayashi et al. |
| 7,209,787 B2 | 4/2007 | Dilorenzo |
| 7,211,050 B1 | 5/2007 | Caplygin |
| 7,216,000 B2 | 5/2007 | Sieracki et al. |
| 7,217,276 B2 | 5/2007 | Henderson |

(56) References Cited

U.S. PATENT DOCUMENTS

| | | | |
|---|---|---|---|
| 7,218,968 B2 | 5/2007 | Condie et al. |
| 7,228,179 B2 | 6/2007 | Campen et al. |
| 7,231,254 B2 | 6/2007 | DiLorenzo |
| 7,236,830 B2 | 6/2007 | Gliner |
| 7,239,910 B2 | 7/2007 | Tanner |
| 7,239,916 B2 | 7/2007 | Thompson et al. |
| 7,239,926 B2 | 7/2007 | Goetz |
| 7,242,984 B2 | 7/2007 | DiLorenzo |
| 7,244,150 B1 | 7/2007 | Brase et al. |
| 7,252,090 B2 | 8/2007 | Goetz |
| 7,254,445 B2 | 8/2007 | Law et al. |
| 7,254,446 B1 | 8/2007 | Erickson |
| 7,257,447 B2 | 8/2007 | Cates et al. |
| 7,266,412 B2 | 9/2007 | Stypulkowski |
| 7,289,761 B2 | 10/2007 | Mazar et al. |
| 7,294,107 B2 | 11/2007 | Simon et al. |
| 7,295,876 B1 | 11/2007 | Erickson |
| 7,299,096 B2 | 11/2007 | Balzer et al. |
| 7,308,302 B1 | 12/2007 | Schuler et al. |
| 7,313,430 B2 | 12/2007 | Urquhart |
| 7,324,851 B1 | 1/2008 | DiLorenzo |
| 7,346,282 B2 | 3/2008 | Sakanaka et al. |
| 7,346,382 B2 | 3/2008 | McIntyre et al. |
| 7,385,443 B1 | 6/2008 | Denison |
| 7,388,974 B2 | 6/2008 | Yanagita |
| 7,437,193 B2 | 10/2008 | Parramon et al. |
| 7,450,997 B1 | 11/2008 | Pianca et al. |
| 7,454,245 B2 | 11/2008 | Armstrong et al. |
| 7,463,928 B2 | 12/2008 | Lee et al. |
| 7,499,048 B2 | 3/2009 | Sieracki et al. |
| 7,499,752 B2 * | 3/2009 | Maschino .......... A61N 1/36082 607/40 |
| 7,505,815 B2 | 3/2009 | Lee et al. |
| 7,532,935 B2 * | 5/2009 | Maschino .......... A61N 1/36082 607/45 |
| 7,548,786 B2 | 6/2009 | Lee et al. |
| 7,555,344 B2 * | 6/2009 | Maschino .......... A61N 1/36082 607/18 |
| 7,565,199 B2 | 7/2009 | Sheffield et al. |
| 7,603,177 B2 | 10/2009 | Sieracki et al. |
| 7,617,002 B2 | 11/2009 | Goetz |
| 7,623,918 B2 | 11/2009 | Goetz |
| 7,650,184 B2 | 1/2010 | Walter |
| 7,657,319 B2 | 2/2010 | Goetz et al. |
| 7,672,734 B2 | 3/2010 | Anderson et al. |
| 7,676,273 B2 | 3/2010 | Goetz et al. |
| 7,680,526 B2 | 3/2010 | McIntyre et al. |
| 7,734,340 B2 | 6/2010 | De Ridder |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,826,902 B2 | 11/2010 | Stone et al. |
| 7,848,802 B2 | 12/2010 | Goetz et al. |
| 7,860,548 B2 | 12/2010 | McIntyre et al. |
| 7,896,808 B2 | 3/2011 | Koh et al. |
| 7,904,134 B2 | 3/2011 | McIntyre et al. |
| 7,945,105 B1 | 5/2011 | Jaenisch |
| 7,949,395 B2 | 5/2011 | Kuzma |
| 7,974,706 B2 | 7/2011 | Moffitt et al. |
| 8,000,794 B2 | 8/2011 | Lozano |
| 8,019,439 B2 | 9/2011 | Kuzma et al. |
| 8,150,524 B2 * | 4/2012 | Maschino .......... A61N 1/36082 607/18 |
| 8,175,710 B2 | 5/2012 | He |
| 8,180,601 B2 | 5/2012 | Butson et al. |
| 8,187,209 B1 | 5/2012 | Giuffrida |
| 8,195,300 B2 | 6/2012 | Gliner et al. |
| 8,209,027 B2 | 6/2012 | Butson et al. |
| 8,224,450 B2 | 7/2012 | Brase |
| 8,257,684 B2 | 9/2012 | Covalin et al. |
| 8,262,714 B2 | 9/2012 | Hulvershorn et al. |
| 8,271,094 B1 | 9/2012 | Moffitt et al. |
| 8,280,514 B2 | 10/2012 | Lozano et al. |
| 8,295,944 B2 | 10/2012 | Howard et al. |
| 8,306,627 B2 | 11/2012 | Armstrong |
| 8,326,433 B2 | 12/2012 | Blum et al. |
| 8,364,278 B2 | 1/2013 | Pianca et al. |
| 8,369,954 B2 | 2/2013 | Stack et al. |
| 8,379,952 B2 | 2/2013 | McIntyre et al. |
| 8,391,985 B2 | 3/2013 | McDonald |
| 8,429,174 B2 | 4/2013 | Ramani et al. |
| 8,452,415 B2 | 5/2013 | Goetz et al. |
| 8,473,061 B2 | 6/2013 | Moffitt et al. |
| 8,483,237 B2 | 7/2013 | Zimmermann et al. |
| 8,543,189 B2 | 9/2013 | Paitel et al. |
| 8,571,665 B2 | 10/2013 | Moffitt et al. |
| 8,589,316 B2 | 11/2013 | Lujan et al. |
| 8,594,800 B2 | 11/2013 | Butson et al. |
| 8,594,801 B2 | 11/2013 | Corndorf et al. |
| 8,606,360 B2 | 12/2013 | Butson et al. |
| 8,620,452 B2 | 12/2013 | King et al. |
| 8,649,845 B2 | 2/2014 | McIntyre et al. |
| 8,675,945 B2 | 3/2014 | Barnhorst et al. |
| 8,679,038 B1 | 3/2014 | Giuffrida |
| 8,688,235 B1 | 4/2014 | Pianca et al. |
| 8,744,596 B2 | 6/2014 | Howard |
| 8,751,008 B2 | 6/2014 | Carlton et al. |
| 8,774,941 B2 | 7/2014 | Pianca |
| 8,792,993 B2 | 7/2014 | Pianca et al. |
| 8,831,731 B2 | 9/2014 | Blum et al. |
| 8,831,742 B2 | 9/2014 | Pianca et al. |
| 8,845,557 B1 | 9/2014 | Giuffrida et al. |
| 8,849,632 B2 | 9/2014 | Sparks et al. |
| 8,855,773 B2 | 10/2014 | Kokones et al. |
| 8,868,199 B2 | 10/2014 | Kaula et al. |
| 8,913,804 B2 | 12/2014 | Blum et al. |
| 8,918,183 B2 | 12/2014 | Carlton et al. |
| 8,918,184 B1 | 12/2014 | Torgerson et al. |
| 8,923,976 B2 | 12/2014 | Johanek |
| 8,958,615 B2 | 2/2015 | Blum et al. |
| 8,972,023 B2 | 3/2015 | Bradley et al. |
| 9,020,789 B2 | 4/2015 | Butson et al. |
| 9,026,217 B2 | 5/2015 | Furukawa et al. |
| 9,050,470 B2 | 6/2015 | Carlton et al. |
| 9,061,138 B2 | 6/2015 | Pianca |
| 9,072,905 B2 | 7/2015 | Kokones et al. |
| 9,081,488 B2 | 7/2015 | Soederstroem |
| 9,084,896 B2 | 7/2015 | Kokones et al. |
| 9,095,266 B1 * | 8/2015 | Fu ........................ G16H 50/20 |
| 9,135,400 B2 | 9/2015 | McIntyre et al. |
| 9,149,630 B2 | 10/2015 | Howard et al. |
| 9,162,056 B2 | 10/2015 | Pianca |
| 9,220,889 B2 | 12/2015 | Carlton et al. |
| 9,227,074 B2 | 1/2016 | Carcieri et al. |
| 9,235,685 B2 | 1/2016 | McIntyre et al. |
| 9,248,272 B2 | 2/2016 | Romero |
| 9,248,296 B2 | 2/2016 | Carcieri et al. |
| 9,254,387 B2 | 2/2016 | Blum et al. |
| 9,272,153 B2 | 3/2016 | Blum et al. |
| 9,289,596 B2 | 3/2016 | Leven |
| 9,289,600 B2 | 3/2016 | Govea et al. |
| 9,302,110 B2 | 4/2016 | Kokones et al. |
| 9,308,372 B2 | 4/2016 | Sparks et al. |
| 9,310,985 B2 | 4/2016 | Blum et al. |
| 9,327,111 B2 | 5/2016 | Pianca et al. |
| 9,358,398 B2 | 6/2016 | Moffitt et al. |
| 9,364,665 B2 | 6/2016 | Bokil et al. |
| 9,381,348 B2 | 7/2016 | Romero et al. |
| 9,387,325 B1 | 7/2016 | Min et al. |
| 9,415,154 B2 | 8/2016 | Leven |
| 9,474,903 B2 | 10/2016 | Chen et al. |
| 9,492,655 B2 | 11/2016 | Pianca et al. |
| 9,498,620 B2 | 11/2016 | Romero et al. |
| 9,526,902 B2 | 12/2016 | Blum et al. |
| 9,566,596 B2 | 2/2017 | Kim et al. |
| 9,572,982 B2 | 2/2017 | Burnes et al. |
| 9,586,053 B2 | 3/2017 | Moffitt et al. |
| 9,592,389 B2 | 3/2017 | Moffitt |
| 9,713,720 B2 | 7/2017 | Zhu |
| 9,775,988 B2 | 10/2017 | Govea et al. |
| 9,792,412 B2 | 10/2017 | Moffitt et al. |
| 9,821,167 B2 | 11/2017 | Carcieri et al. |
| 9,925,382 B2 | 3/2018 | Carlton et al. |

(56) References Cited

U.S. PATENT DOCUMENTS

| | | | |
|---|---|---|---|
| 9,959,940 B2 | 5/2018 | Moffitt et al. |
| 9,974,959 B2 | 5/2018 | Moffitt et al. |
| 10,067,659 B2 | 9/2018 | Bokil |
| 10,071,249 B2 | 9/2018 | Zottola |
| 10,086,205 B2 | 10/2018 | Grill et al. |
| 10,213,148 B2 | 2/2019 | Min et al. |
| 10,265,528 B2 | 4/2019 | Carcieri et al. |
| 10,265,531 B2 | 4/2019 | Bokil |
| 10,286,205 B2 | 5/2019 | Steinke et al. |
| 10,300,282 B2 | 5/2019 | Torgerson et al. |
| 10,335,607 B2 | 7/2019 | Orinski |
| 10,357,657 B2 | 7/2019 | Moffitt et al. |
| 10,369,364 B2 | 8/2019 | Moffitt et al. |
| 10,463,860 B2 * | 11/2019 | Sinclair .............. A61B 5/4842 |
| 10,485,969 B2 | 11/2019 | Govea et al. |
| 10,493,269 B2 | 12/2019 | Stoffregen et al. |
| 10,525,257 B2 | 1/2020 | Govea et al. |
| 10,525,266 B2 | 1/2020 | Moffitt et al. |
| 10,603,498 B2 | 3/2020 | Blum et al. |
| 10,625,072 B2 | 4/2020 | Serrano Carmona |
| 10,631,937 B2 | 4/2020 | Tyulmankov et al. |
| 10,639,488 B2 | 5/2020 | Kalgren et al. |
| 10,653,330 B2 | 5/2020 | Angle et al. |
| 10,675,468 B2 | 6/2020 | Torgerson |
| 10,716,505 B2 | 7/2020 | Blum et al. |
| 10,780,282 B2 | 9/2020 | Mustakos et al. |
| 10,814,127 B2 | 10/2020 | Nageri et al. |
| 10,814,140 B2 | 10/2020 | Zhang et al. |
| 10,850,101 B2 | 12/2020 | Zhang et al. |
| 10,960,203 B2 | 3/2021 | Tyler et al. |
| 11,020,052 B2 | 6/2021 | Zuckerman-Stark et al. |
| 11,185,697 B2 * | 11/2021 | Sinclair .............. A61B 5/6868 |
| 11,278,726 B2 * | 3/2022 | Sinclair .............. A61N 1/36167 |
| 11,285,329 B2 | 3/2022 | Carcieri et al. |
| 11,298,550 B2 | 4/2022 | Howard et al. |
| 11,357,986 B2 | 6/2022 | Steinke et al. |
| 11,517,755 B2 | 12/2022 | Zhang et al. |
| 11,707,622 B2 | 7/2023 | Juarez Paz et al. |
| 11,745,010 B2 | 9/2023 | Donega et al. |
| 11,890,478 B2 * | 2/2024 | Sinclair .............. A61B 5/377 |
| 2001/0031071 A1 | 10/2001 | Nichols et al. |
| 2002/0032375 A1 | 3/2002 | Bauch et al. |
| 2002/0062143 A1 | 5/2002 | Baudino et al. |
| 2002/0087201 A1 | 7/2002 | Firlik et al. |
| 2002/0099295 A1 | 7/2002 | Gil et al. |
| 2002/0115603 A1 | 8/2002 | Whitehouse |
| 2002/0116030 A1 | 8/2002 | Rezei |
| 2002/0123780 A1 | 9/2002 | Grill et al. |
| 2002/0128694 A1 | 9/2002 | Holsheimer |
| 2002/0151939 A1 | 10/2002 | Rezai |
| 2002/0183607 A1 | 12/2002 | Bauch et al. |
| 2002/0183740 A1 | 12/2002 | Edwards et al. |
| 2002/0183817 A1 | 12/2002 | Van Venrooij et al. |
| 2003/0097159 A1 | 5/2003 | Schiff et al. |
| 2003/0149450 A1 | 8/2003 | Mayberg |
| 2003/0171791 A1 | 9/2003 | KenKnight et al. |
| 2003/0212439 A1 | 11/2003 | Schuler et al. |
| 2004/0034394 A1 | 2/2004 | Woods et al. |
| 2004/0044279 A1 | 3/2004 | Lewin et al. |
| 2004/0044378 A1 | 3/2004 | Holsheimer |
| 2004/0044379 A1 | 3/2004 | Holsheimer |
| 2004/0054297 A1 | 3/2004 | Wingeier et al. |
| 2004/0059395 A1 | 3/2004 | North et al. |
| 2004/0106916 A1 | 6/2004 | Quaid et al. |
| 2004/0133248 A1 | 7/2004 | Frei et al. |
| 2004/0152957 A1 | 8/2004 | Stivoric et al. |
| 2004/0181262 A1 | 9/2004 | Bauhahn |
| 2004/0186532 A1 | 9/2004 | Tadlock |
| 2004/0193231 A1 | 9/2004 | David et al. |
| 2004/0199216 A1 | 10/2004 | Lee et al. |
| 2004/0267330 A1 | 12/2004 | Lee et al. |
| 2005/0003396 A1 * | 1/2005 | Ozkan .............. C12Q 1/6825 435/7.1 |
| 2005/0021090 A1 | 1/2005 | Schuler et al. |
| 2005/0033380 A1 | 2/2005 | Tanner et al. |
| 2005/0049649 A1 | 3/2005 | Luders et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0075689 A1 | 4/2005 | Toy et al. |
| 2005/0085714 A1 | 4/2005 | Foley et al. |
| 2005/0165294 A1 | 7/2005 | Weiss |
| 2005/0171587 A1 | 8/2005 | Daglow et al. |
| 2005/0228250 A1 | 10/2005 | Bitter et al. |
| 2005/0251061 A1 | 11/2005 | Schuler et al. |
| 2005/0261061 A1 | 11/2005 | Nguyen et al. |
| 2005/0261601 A1 | 11/2005 | Schuler et al. |
| 2005/0261747 A1 | 11/2005 | Schuler et al. |
| 2005/0267347 A1 | 12/2005 | Oster |
| 2005/0288732 A1 | 12/2005 | Schuler et al. |
| 2006/0004422 A1 | 1/2006 | De Ridder |
| 2006/0017749 A1 | 1/2006 | McIntyre et al. |
| 2006/0020292 A1 | 1/2006 | Goetz et al. |
| 2006/0069415 A1 | 3/2006 | Cameron et al. |
| 2006/0094951 A1 | 5/2006 | Dean et al. |
| 2006/0095088 A1 | 5/2006 | De Riddler |
| 2006/0155340 A1 | 7/2006 | Schuler et al. |
| 2006/0206169 A1 | 9/2006 | Schuler |
| 2006/0218007 A1 | 9/2006 | Bjorner et al. |
| 2006/0224189 A1 | 10/2006 | Schuler et al. |
| 2006/0235472 A1 | 10/2006 | Goetz et al. |
| 2006/0259079 A1 | 11/2006 | King |
| 2006/0259099 A1 | 11/2006 | Goetz et al. |
| 2007/0000372 A1 | 1/2007 | Rezai et al. |
| 2007/0017749 A1 | 1/2007 | Dold et al. |
| 2007/0027499 A1 * | 2/2007 | Maschino .......... A61N 1/36096 607/45 |
| 2007/0027514 A1 | 2/2007 | Gerber |
| 2007/0043268 A1 | 2/2007 | Russell |
| 2007/0049817 A1 | 3/2007 | Preiss et al. |
| 2007/0067003 A1 | 3/2007 | Sanchez et al. |
| 2007/0078498 A1 | 4/2007 | Rezai et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0135855 A1 | 6/2007 | Foshee et al. |
| 2007/0150036 A1 | 6/2007 | Anderson |
| 2007/0156186 A1 | 7/2007 | Lee et al. |
| 2007/0162086 A1 | 7/2007 | DiLorenzo |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0179557 A1 | 8/2007 | Maschino et al. |
| 2007/0185544 A1 | 8/2007 | Dawant et al. |
| 2007/0191887 A1 | 8/2007 | Schuler et al. |
| 2007/0191912 A1 | 8/2007 | Ficher et al. |
| 2007/0197891 A1 | 8/2007 | Shachar et al. |
| 2007/0203450 A1 | 8/2007 | Berry |
| 2007/0203532 A1 | 8/2007 | Tass et al. |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0260283 A1 | 11/2007 | Li |
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0046037 A1 | 2/2008 | Haubrich et al. |
| 2008/0071150 A1 | 3/2008 | Miesel et al. |
| 2008/0081982 A1 | 4/2008 | Simon et al. |

(56) References Cited

U.S. PATENT DOCUMENTS

| | | |
|---|---|---|
| 2008/0086451 A1 | 4/2008 | Torres et al. |
| 2008/0091248 A1 | 4/2008 | Libbus et al. |
| 2008/0103533 A1 | 5/2008 | Patel et al. |
| 2008/0114233 A1 | 5/2008 | McIntyre et al. |
| 2008/0114579 A1 | 5/2008 | McIntyre et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0154341 A1 | 6/2008 | McIntyre et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215101 A1 | 9/2008 | Rezai et al. |
| 2008/0215118 A1 | 9/2008 | Goetz et al. |
| 2008/0227139 A1 | 9/2008 | Deisseroth et al. |
| 2008/0238749 A1 | 10/2008 | Comdorf |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0054947 A1 | 2/2009 | Bourn et al. |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0163975 A1 | 6/2009 | Gerber et al. |
| 2009/0187222 A1 | 7/2009 | Barker |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1 | 8/2009 | McIntyre et al. |
| 2009/0228073 A1 | 9/2009 | Scholten |
| 2009/0242399 A1 | 10/2009 | Kamath et al. |
| 2009/0270949 A1 | 10/2009 | Kalpin et al. |
| 2009/0276008 A1 | 11/2009 | Lee et al. |
| 2009/0276021 A1 | 11/2009 | Meadows et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010387 A1 | 1/2010 | Skelton et al. |
| 2010/0010432 A1 | 1/2010 | Skelton |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1 | 2/2010 | Goetz |
| 2010/0057161 A1 | 3/2010 | Machado et al. |
| 2010/0064249 A1 | 3/2010 | Groetken |
| 2010/0076535 A1 | 3/2010 | Pianca et al. |
| 2010/0113959 A1 | 5/2010 | Pascual-Leon et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kuala et al. |
| 2010/0152807 A1 | 6/2010 | Grill et al. |
| 2010/0179562 A1 | 7/2010 | Linker et al. |
| 2010/0211135 A1 | 8/2010 | Caparso et al. |
| 2010/0268298 A1 | 10/2010 | Moffitt |
| 2010/0324410 A1 | 12/2010 | Paek et al. |
| 2010/0331883 A1 | 12/2010 | Schmitz et al. |
| 2011/0004267 A1 | 1/2011 | Meadows |
| 2011/0005069 A1 | 1/2011 | Pianca |
| 2011/0040351 A1 | 2/2011 | Buston et al. |
| 2011/0054559 A1 | 3/2011 | Rosenberg et al. |
| 2011/0066407 A1 | 3/2011 | Butson et al. |
| 2011/0078900 A1 | 4/2011 | Pianca et al. |
| 2011/0093045 A1 | 4/2011 | Moffitt |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0137372 A1 | 6/2011 | Makous et al. |
| 2011/0160796 A1 | 6/2011 | Lane et al. |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0224665 A1 | 9/2011 | Crosby et al. |
| 2011/0238129 A1 | 9/2011 | Moffitt |
| 2011/0251583 A1 | 10/2011 | Miyazawa et al. |
| 2011/0270348 A1 | 11/2011 | Goetz |
| 2011/0306845 A1 | 12/2011 | Osorio |
| 2011/0306846 A1 | 12/2011 | Osorio |
| 2011/0307032 A1 | 12/2011 | Goetz et al. |
| 2011/0313485 A1 | 12/2011 | DeMulling et al. |
| 2011/0313500 A1 | 12/2011 | Barker et al. |
| 2012/0016378 A1 | 1/2012 | Pianca et al. |
| 2012/0027272 A1 | 2/2012 | Akinyemi et al. |
| 2012/0046710 A1 | 2/2012 | Digiore et al. |
| 2012/0046715 A1 | 2/2012 | Moffitt et al. |
| 2012/0071949 A1 | 3/2012 | Pianca et al. |
| 2012/0078106 A1 | 3/2012 | Dentinger et al. |
| 2012/0089205 A1 | 4/2012 | Boyden et al. |
| 2012/0101552 A1 | 4/2012 | Lazarewicz et al. |
| 2012/0116476 A1 | 5/2012 | Kothandaraman |
| 2012/0165898 A1 | 6/2012 | Moffitt |
| 2012/0165901 A1 | 6/2012 | Zhu et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0239109 A1 | 9/2012 | Lee |
| 2012/0239115 A1 | 9/2012 | Lee |
| 2012/0265103 A1 | 10/2012 | Policker et al. |
| 2012/0265262 A1 | 10/2012 | Osorio |
| 2012/0265268 A1 | 10/2012 | Blum et al. |
| 2012/0271189 A1 | 10/2012 | Nelson et al. |
| 2012/0277833 A1 | 11/2012 | Gerber et al. |
| 2012/0296396 A1* | 11/2012 | Moffitt .................. G16H 20/30 607/59 |
| 2012/0302912 A1 | 11/2012 | Moffitt et al. |
| 2012/0303087 A1 | 11/2012 | Moffitt et al. |
| 2012/0303098 A1 | 11/2012 | Perryman |
| 2012/0314919 A1 | 12/2012 | Sparks et al. |
| 2012/0314924 A1 | 12/2012 | Carlton et al. |
| 2012/0316615 A1 | 12/2012 | Digiore et al. |
| 2012/0316619 A1 | 12/2012 | Goetz et al. |
| 2012/0330374 A1 | 12/2012 | Blum et al. |
| 2012/0330622 A1 | 12/2012 | Butson et al. |
| 2013/0035740 A1 | 2/2013 | Sharma et al. |
| 2013/0039550 A1 | 2/2013 | Blum et al. |
| 2013/0053926 A1 | 2/2013 | Hincapie Ordonez et al. |
| 2013/0060305 A1 | 3/2013 | Bokil |
| 2013/0105071 A1 | 5/2013 | Digiore et al. |
| 2013/0116744 A1 | 5/2013 | Blum et al. |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2013/0150922 A1 | 6/2013 | Butson et al. |
| 2013/0197424 A1 | 8/2013 | Bedenbaugh |
| 2013/0197602 A1 | 8/2013 | Pianca et al. |

(56) References Cited

U.S. PATENT DOCUMENTS

| | | |
|---|---|---|
| 2013/0226261 A1 | 8/2013 | Sparks et al. |
| 2013/0245722 A1 | 9/2013 | Ternes et al. |
| 2013/0261684 A1 | 10/2013 | Howard |
| 2013/0289380 A1 | 10/2013 | Molnar et al. |
| 2013/0289660 A1 | 10/2013 | Molnar et al. |
| 2013/0317572 A1 | 11/2013 | Zhu et al. |
| 2013/0317573 A1 | 11/2013 | Zhu et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0063017 A1 | 3/2014 | Kaula et al. |
| 2014/0066999 A1 | 3/2014 | Carcieri et al. |
| 2014/0067018 A1 | 3/2014 | Carcieri et al. |
| 2014/0067022 A1 | 3/2014 | Carcieri et al. |
| 2014/0074180 A1 | 3/2014 | Heldman et al. |
| 2014/0107731 A1 | 4/2014 | Stone et al. |
| 2014/0122379 A1 | 5/2014 | Moffitt et al. |
| 2014/0200633 A1 | 7/2014 | Moffitt |
| 2014/0243926 A1 | 8/2014 | Carcieri |
| 2014/0276707 A1 | 9/2014 | Jaax |
| 2014/0277282 A1 | 9/2014 | Jaax |
| 2014/0277284 A1 | 9/2014 | Chen et al. |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0134031 A1 | 5/2015 | Moffitt et al. |
| 2015/0151113 A1 | 6/2015 | Govea et al. |
| 2015/0246231 A1 | 9/2015 | Martens et al. |
| 2015/0360039 A1 | 12/2015 | Lempka et al. |
| 2016/0001087 A1 | 1/2016 | Moffitt |
| 2016/0022995 A1 | 1/2016 | Kothandaraman et al. |
| 2016/0023008 A1 | 1/2016 | Kothandaraman |
| 2016/0030749 A1 | 2/2016 | Carcieri et al. |
| 2016/0030750 A1 | 2/2016 | Bokil et al. |
| 2016/0045748 A1 | 2/2016 | Astrom et al. |
| 2016/0082252 A1 | 3/2016 | Hershey et al. |
| 2016/0096025 A1 | 4/2016 | Moffitt et al. |
| 2016/0136429 A1 | 5/2016 | Massoumi et al. |
| 2016/0136443 A1 | 5/2016 | Kothandaraman et al. |
| 2016/0144186 A1 | 5/2016 | Kaemmerer et al. |
| 2016/0175594 A1 | 6/2016 | Min et al. |
| 2016/0206380 A1 | 7/2016 | Sparks et al. |
| 2016/0228692 A1 | 8/2016 | Steinke et al. |
| 2016/0256691 A1 | 9/2016 | Cecchi et al. |
| 2016/0256693 A1 | 9/2016 | Parramon |
| 2016/0346557 A1 | 12/2016 | Bokil |
| 2016/0375248 A1 | 12/2016 | Carcieri et al. |
| 2016/0375258 A1 | 12/2016 | Steinke |
| 2017/0100593 A1 | 4/2017 | Zottola |
| 2017/0100601 A1 | 4/2017 | Xiao et al. |
| 2017/0106197 A1 | 4/2017 | Wechter et al. |
| 2017/0197086 A1 | 7/2017 | Howard et al. |
| 2017/0225007 A1 | 8/2017 | Orinski |
| 2017/0252570 A1 | 9/2017 | Serrano Carmona et al. |
| 2017/0259078 A1 | 9/2017 | Howard |
| 2017/0304610 A1 | 10/2017 | Huibregtse et al. |
| 2017/0304633 A1 | 10/2017 | Zhang |
| 2017/0372039 A1 | 12/2017 | Mustakos et al. |
| 2018/0064930 A1 | 3/2018 | Zhang et al. |
| 2018/0078776 A1 | 3/2018 | Mustakos et al. |
| 2018/0104482 A1 | 4/2018 | Bokil |
| 2018/0104500 A1 | 4/2018 | Blum et al. |
| 2018/0110971 A1 | 4/2018 | Serrano Carmona |
| 2018/0185650 A1 | 7/2018 | Shah |
| 2018/0193655 A1 | 7/2018 | Zhang et al. |
| 2018/0214700 A1 | 8/2018 | Vansickle et al. |
| 2018/0264278 A1 | 9/2018 | Laghi |
| 2018/0272142 A1 | 9/2018 | Zhang et al. |
| 2018/0280698 A1 | 10/2018 | Steinke et al. |
| 2018/0296828 A1 | 10/2018 | Bradley et al. |
| 2018/0369589 A1 | 12/2018 | Schouenborg |
| 2018/0369606 A1 | 12/2018 | Zhang et al. |
| 2018/0369607 A1 | 12/2018 | Zhang et al. |
| 2019/0015660 A1 | 1/2019 | Zhang et al. |
| 2019/0184171 A1 | 6/2019 | Mustakos et al. |
| 2019/0209834 A1 | 7/2019 | Zhang et al. |
| 2019/0209849 A1 | 7/2019 | Hershey et al. |
| 2019/0262609 A1 | 8/2019 | Brill et al. |
| 2019/0275331 A1 | 9/2019 | Zhu |
| 2019/0329047 A1 | 10/2019 | Moffitt et al. |
| 2019/0329049 A1 | 10/2019 | Carcieri et al. |
| 2020/0094047 A1 | 3/2020 | Govea et al. |
| 2020/0139127 A1 | 5/2020 | Zhang et al. |
| 2020/0155854 A1 | 5/2020 | Leven et al. |
| 2020/0155859 A1 | 5/2020 | Blum et al. |
| 2020/0171298 A1 | 6/2020 | Goetz et al. |
| 2020/0171310 A1 | 6/2020 | Walter et al. |
| 2020/0179600 A1 | 6/2020 | Zanos et al. |
| 2020/0222704 A1 | 7/2020 | Moffitt et al. |
| 2020/0269053 A1 | 8/2020 | Park |
| 2020/0353254 A1 | 11/2020 | O Laighin et al. |
| 2020/0376262 A1 | 12/2020 | Clark et al. |
| 2020/0376263 A1 | 12/2020 | Zhu |
| 2020/0398057 A1 | 12/2020 | Esteller et al. |
| 2021/0008388 A1 | 1/2021 | Vansickle et al. |
| 2021/0008389 A1 | 1/2021 | Featherstone et al. |
| 2021/0016111 A1 | 1/2021 | Vansickle et al. |
| 2021/0023374 A1 | 1/2021 | Block et al. |
| 2021/0052893 A1 | 2/2021 | Suri et al. |
| 2021/0106830 A1* | 4/2021 | Provenza ................ A61B 5/37 |
| 2021/0113844 A1 | 4/2021 | Zhang et al. |
| 2021/0128920 A1 | 5/2021 | Grill et al. |
| 2021/0196956 A1 | 7/2021 | Juárez Paz |
| 2021/0196964 A1 | 7/2021 | Schnell et al. |
| 2021/0205613 A1 | 7/2021 | Bradley et al. |
| 2021/0268268 A1 | 9/2021 | Horn et al. |
| 2021/0275820 A1 | 9/2021 | Grill, Jr. et al. |
| 2021/0387002 A1 | 12/2021 | Bourget et al. |
| 2022/0007980 A1 | 1/2022 | Single |
| 2022/0008729 A1 | 1/2022 | Zhu |
| 2022/0040485 A1 | 2/2022 | Li et al. |
| 2022/0062640 A1 | 3/2022 | Raike et al. |
| 2022/0072329 A1 | 3/2022 | Howard |
| 2022/0126100 A1 | 4/2022 | Jackson et al. |
| 2022/0257950 A1 | 8/2022 | Moore et al. |
| 2022/0266026 A1 | 8/2022 | Case et al. |
| 2022/0296892 A1 | 9/2022 | Esteller et al. |
| 2022/0296893 A1 | 9/2022 | Steinke et al. |
| 2022/0339448 A1 | 10/2022 | Jayakumar et al. |
| 2022/0347479 A1 | 11/2022 | Esteller et al. |
| 2022/0355114 A1 | 11/2022 | Moore et al. |
| 2022/0355115 A1 | 11/2022 | Moore et al. |
| 2022/0370808 A1 | 11/2022 | Esteller |
| 2022/0387785 A1 | 12/2022 | Huynh et al. |
| 2022/0395690 A1 | 12/2022 | Haddock et al. |
| 2023/0048571 A1 | 2/2023 | Poltorak |
| 2023/0064552 A1 | 3/2023 | Moffitt |
| 2023/0141183 A1 | 5/2023 | Moore et al. |
| 2023/0181089 A1 | 6/2023 | Zhang et al. |
| 2023/0181090 A1 | 6/2023 | Juarez Paz |
| 2023/0181906 A1 | 6/2023 | Moore et al. |
| 2023/0248977 A1 | 8/2023 | Esteller et al. |
| 2023/0264025 A1 | 8/2023 | Malekmohammadi et al. |
| 2023/0271015 A1 | 8/2023 | Malekmohammadi et al. |
| 2023/0277854 A1 | 9/2023 | Gaviao Kilmar |
| 2024/0065620 A1 | 2/2024 | Moore et al. |
| 2024/0157151 A1 | 5/2024 | Juarez Paz |
| 2024/0198110 A1 | 6/2024 | Moore |
| 2024/0316346 A1 | 9/2024 | Shah et al. |

FOREIGN PATENT DOCUMENTS

| | | |
|---|---|---|
| EP | 1166819 | 1/2002 |
| EP | 1372780 | 1/2004 |

(56) References Cited

FOREIGN PATENT DOCUMENTS

| | | |
|---|---|---|
| EP | 1559369 | 8/2005 |
| WO | 97/39797 | 10/1997 |
| WO | 98/48880 | 11/1998 |
| WO | 01/90876 | 11/2001 |
| WO | 02/26314 | 4/2002 |
| WO | 02/28473 | 4/2002 |
| WO | 02/065896 | 8/2002 |
| WO | 02/072192 | 9/2002 |
| WO | 03/086185 | 10/2003 |
| WO | 2004/019799 A2 | 3/2004 |
| WO | 2004041080 | 5/2005 |
| WO | 2006017053 | 2/2006 |
| WO | 2006113305 | 10/2006 |
| WO | 20071097859 | 8/2007 |
| WO | 20071097861 A1 | 8/2007 |
| WO | 2007/100427 | 9/2007 |
| WO | 2007/100428 | 9/2007 |
| WO | 2007/112061 | 10/2007 |
| WO | 2009097224 | 8/2009 |
| WO | 2010/109448 | 9/2010 |
| WO | 2010/120823 A2 | 10/2010 |
| WO | 2011025865 | 3/2011 |
| WO | 2011/139779 A1 | 11/2011 |
| WO | 2011/159688 A2 | 12/2011 |
| WO | 2012088482 | 6/2012 |
| WO | 2014/076698 | 5/2014 |
| WO | 2016/025913 | 2/2016 |
| WO | 2016081099 | 5/2016 |
| WO | 2016112398 | 7/2016 |

OTHER PUBLICATIONS

Mcintyre, Cameron C., et al., "Electric field generated by deep brain stimulation of the subthalamic nucleus," Biomedical Engineering Society Annual Meeting, Nashville TN (Oct. 2003), 16 pages.

Mcintyre, Cameron C., et al., "Excitation of central nervous system neurons by nonuniform electric fields," Biophys. J., 76(2) (1999), pp. 878-888.

McNeal, DR., et al., "Analysis of a model for excitation of myelinated nerve," IEEE Trans Biomed Eng., vol. 23 (1976), pp. 329-337.

Micheli-Tzanakou, E. , et al., "Computational Intelligence for target assesment in Parkinson's disease," Proceedings of SPIE vol. 4479, Applications and Science of Neural Networks, Fuzzy Systems, and Evolutionary Computation IV (2001 ), pp. 54-69.

Miocinovic, S., et al., "Computational analysis of subthalamic nucleus and lenticular fasciculus activation during therapeutic deep brain stimulation," J Neurophysiol., 96(3) (Sep. 2006), pp. 1569-1580.

Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001 ), p. 1540.

Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Engineering, 50(9) (Sep. 2003), pp. 1074-1085.

Moffitt, MA., et al., "Prediction of myelinated nerve fiber stimulation thresholds: limitations of linear models," IEEE Transactions on Biomedical Engineering, 51 (2) (2003), pp. 229-236.

Moro, E, et al., "The impact on Parkinson's disease of electrical parameter settings in STN stimulation," Neurology, 59(5) (Sep. 10, 2002), pp. 706-713.

Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.

Nowak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.

O'Suilleabhain, PE., et al., "Tremor response to polarity, voltage, pulsewidth and frequency of thalamic stimulation," Neurology, 60(5) (Mar. 11, 2003), pp. 786-790.

Pierpaoli, C., et al., "Toward a quantitative assessment of diffusion anisotropy," Magn Reson Med., 36(6) (Dec. 1996), pp. 893-906.

Plonsey, R., et al., "Considerations of quasi-stationarity in electrophysiological systems," Bull Math Biophys., 29(4) (Dec. 1967), pp. 657-664.

Ranck, J B., "Specific impedance of rabbit cerebral cortex," Exp. Neurol., vol. 7 (Feb. 1963), pp. 144-152.

Ranck, J B., et al., "The Specific impedance of the dorsal columns of the cat: an anisotropic medium," Exp. Neurol., 11 (Apr. 1965), pp. 451-463.

Ranck, J B., "Which elements are excited in electrical stimulation of mammalian central nervous system: a review," Brain Res., 98(3) (Nov. 21, 1975), pp. 417-440.

Rattay, F., et al., "A model of the electrically excited human cochlear neuron. I. Contribution of neural substructures to the generation and propagation of spikes," Hear Res., 153(1-2) (Mar. 2001), pp. 43-63.

Rattay, F., "A model of the electrically excited human cochlear neuron. II. Influence of the three-dimensional cochlear structure on neural excitability," Hear Res., 153(1-2) (Mar. 2001), pp. 64-79.

Rattay, F., "Arrival at Functional Electrostimulation by modelling of fiber excitation," Proceedings of the Ninth annual Conference of the IEEE Engineering in Medicine and Biology Society (1987), pp. 1459-1460.

Rattay, F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.

Rizzone, M., et al., "Deep brain stimulation of the subthalamic nucleus in Parkinson's disease: effects of variation in stimulation parameters," J. Neurol. Neurosurg. Psychiatry., 71(2) (Aug. 2001), pp. 215-219.

Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.

Sances, A., et al., "In Electroanesthesia: Biomedical and Biophysical Studies," A Sances and SJ Larson, Eds., Academic Press, NY (1975), pp. 114-124.

Si. Jean, P., et al., "Automated atlas integration and interactive three-dimensional visualization tools for planning and guidance in functional neurosurgery," IEEE Transactions on Medical Imaging, 17(5) (1998), pp. 672-680.

Starr, P. A., et al., "Implantation of deep brain stimulators into the subthalamic nucleus: technical approach and magnetic resonance imaging-verified lead locations," J. Neurosurg., 97(2) (Aug. 2002), pp. 370-387.

Sterio, D., et al., "Neurophysiological refinement of subthalamic nucleus targeting," Neurosurgery, 50(1) (Jan. 2002), pp. 58-69.

Struijk, J. J., et al., "Excitation of dorsal root fibers in spinal cord stimulation: a theoretical study," IEEE Transactions on Biomedical Engineering, 40(7) (Jul. 1993), pp. 632-639.

Struijk, J J., et al., "Recruitment of dorsal column fibers in spinal cord stimulation: influence of collateral branching," IEEE Transactions on Biomedical Engineering, 39(9) (Sep. 1992), pp. 903-912.

Tamma, F., et al., "Anatomo-clinical correlation of intraoperative stimulation-induced side effects during HF-DBS of the subthalamic nucleus," Neurol Sci., vol. 23 (Suppl 2) (2002), pp. 109-110.

Tarler, M., et al., "Comparison between monopolar and tripolar configurations in chronically implanted nerve cuff electrodes," IEEE 17th Annual Conference Engineering in Medicine and Biology Society, vol. 2 (1995), pp. 1093-1109.

Testerman, Roy L., "Coritical response to callosal stimulation: A model for determining safe and efficient stimulus parameters," Annals of Biomedical Engineering, 6(4) (1978), pp. 438-452.

Tuch, D.S., et al., "Conductivity mapping of biological tissue using diffusion MRI," Ann NY Acad Sci., 888 (Oct. 30, 1999), pp. 314-316.

(56) References Cited

OTHER PUBLICATIONS

Tuch, D.S., et al., "Conductivity tensor mapping of the human brain using diffusion tensor MRI," Proc Nall Acad Sci USA, 98(20) (Sep. 25, 2001), pp. 11697-11701.
Veraart, C., et al., "Selective control of muscle activation with a multipolar nerve cuff electrode," IEEE Transactions on Biomedical Engineering, 40(7) (Jul. 1993), pp. 640-653.
Vercueil, L., et al., "Deep brain stimulation in the treatment of severe dystonia," J. Neurol., 248(8) (Aug. 2001 ), pp. 695-700.
Vilalte, "Circuit Design of the Power-on-Reset," Apr. 2000, pp. 1-25.
Vitek, J. L., "Mechanisms of deep brain stimulation: excitation or inhibition," Mov. Disord., vol. 17 (Suppl. 3) (2002), pp. 69-72.
Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.
Wakana, S., et al., "Fiber tract-based atlas of human white matter anatomy," Radiology, 230(1) (Jan. 2004), pp. 77-87.
Alexander, DC., et al., "Spatial transformations of diffusion tensor magnetic resonance images," IEEE Transactions on Medical Imaging, 20 (11), (2001), pp. 1131-1139.
Wu, Y. R., et al., "Does Stimulation of the GPi control dyskinesia by activating inhibitory axons?," Mov. Disord., vol. 16 (2001), pp. 208-216.
Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.
Yianni, John, et al., "Globus pallidus internus deep brain stimulation for dystonic conditions: a prospective audit," Mov. Disord., vol. 18 (2003), pp. 436-442.
Zonenshayn, M., et al., "Comparison of anatomic and neurophysiological methods for subthalamic nucleus targeting," Neurosurgery, 47(2) (Aug. 2000), pp. 282-294.
Voghell et al., "Programmable Current Source Dedicated to Implantable Microstimulators" ICM '98 Proceedings of the Tenth International Conference, pp. 67-70.
Butson, Christopher R., et al., "Patient-specific analysis of the volume of tissue activated during deep brain stimulation", NeuroImage. vol. 34. (2007),661-670.
Adler, DE., et al., "The tentorial notch: anatomical variation, morphometric analysis, and classification in 100 human autopsy cases," J. Neurosurg., 96(6), (Jun. 2002), pp. 1103-1112.
Jones et al., "An Advanced Demultiplexing System for Physiological Stimulation", IEEE Transactions on Biomedical Engineering, vol. 44 No. 12 Dec. 1997, pp. 1210-1220.
McIntyre, Cameron , et al., "Finite element analysis of the current-density and electric field generated by metal microelectrodes", Ann Biomed Eng . 29(3), (2001 ),227-235.
Foster, K. R., et al., "Dielectric properties of tissues and biological materials: a critical review.", Grit Rev Biomed Ena. 17(1 ). {1989),25-104.
Limousin, P., et al., "Electrical stimulation of the subthalamic nucleus in advanced Parkinson's disease", N Engl J Med .. 339(16), (Oct. 15, 1998), 1105-11.
Kitagawa, M., et al., "Two-year follow-up of chronic stimulation of the posterior subthalamic white matter for tremor-dominant Parkinson's disease.", Neurosurgery. 56(2). (Feb. 2005),281-9.
Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation Engineering (2005), 160-165.
Holsheimer, J. , et al., "Chronaxie calculated from current-duration and voltage-duration data", J Neurosci Methods. 97(1). (Apr. 1, 2000),45-50.
Hines, M. L., et al., "The Neuron simulation environment", Neural Comput. 9(6). (Aug. 15, 1997), 1179-209.
Herzog, J., et al., "Most effective stimulation site in subthalamic deep brain stimulation for Parkinson's disease", Mov Disord. 19(9). (Sep. 2004),1050-4.
Hershey, T., et al., "Cortical and subcortical blood flow effects of subthalamic nucleus stimulation in PD.", Neurology 61(6). (Sep. 23, 2003),816-21.
Hemm, S. , et al., "Evolution of Brain Impedance in Dystonic Patients Treated by GPi Electrical Stimulation", Neuromodulation 7(2) (Apr. 2004),67-75.
Hemm, S., et al., "Deep brain stimulation in movement disorders: stereotactic coregistration of two-dimensional electrical field modeling and magnetic resonance imaging.", J Neurosurg. 103(6): (Dec. 2005),949-55.
Haueisen, J, et al., "The influence of brain tissue anisotropy on human EEG and MEG", Neuroimage 15(1) (Jan. 2002),159-166.
Haslinger, B., et al., "Frequency-correlated decreases of motor cortex activity associated with subthalamic nucleus stimulation in Parkinson's disease.", Neuroimage 28(3). (Nov. 15, 2005),598-606.
Hashimoto, T. , et al., "Stimulation of the subthalamic nucleus changes the firing pattern of pallidal neurons", J Neurosci. 23(5). (Mar. 1, 2003),1916-23.
Hardman, C. D., et al., "Comparison of the basal ganglia in rats, marmosets, macaques, baboons, and humans: volume and neuronal number for the output, internal relay, and striatal modulating nuclei", J Comp Neurol., 445(3). (Apr. 8, 2002),238-55.
McNaughtan et al., "Electrochemical Issues in Impedance Tomography", 1st World Congress on Industrial Process Tomography, Buxton, Greater Manchester, Apr. 14-17, 1999.
Grill, Wm., et al., "Electrical properties of implant encapsulation tissue", Ann Biomed Eng. vol. 22. (1994),23-33.
Grill, W. M., et al., "Deep brain stimulation creates an informational lesion of the stimulated nucleus", Neuroreport. 15I7t (May 19, 2004 ), 1137-40.
International Search Report and Written Opinion for PCT Application No. PCT/US2022/033226 mailed Sep. 20, 2022.
Pulliam CL, Heldman DA, Orcutt TH, Mera TO, Giuffrida JP, Vitek JL. Motion sensor strategies for automated optimization of deep brain stimulation in Parkinson's disease. Parkinsonism Relat Disord. Apr. 2015; 21(4):378-82.
Benoit M. Dawant et al: "The VU-DBS project: integrated and computer-assisted planning, intra-operative placement, and post-operative programming of deep-brain stimulators", Proceedings of SPIE, vol. 6509, Mar. 6, 2007 (Mar. 6, 2007), 11 pages.
Nowinski, W. L., et al., "Statistical analysis of 168 bilateral subthalamic nucleus implantations by means of the probabilistic functional atlas.", Neurosurgery 57(4 Suppl) (Oct. 2005),319-30.
Obeso, J. A., et al., "Deep-brain stimulation of the subthalamic nucleus or the pars interna of the globus pallidus in Parkinson's disease.", N Engl J Med., 345{13l. The Deep-Brain Stimulation for Parkinson's Disease Study Group, (Sep. 27, 2001 ),956-63.
Butson et al.. "Current Steering to control the volume of tissue activated during deep brain stimulation," vol. 1, No. 1, Dec. 3, 2007, pp. 7-15.
Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001),31-41.
Phillips, M. D., et al., "Parkinson disease: pattern of functional MR imaging activation during deep brain stimulation of subthalamic nucleus-initial experience", Radiology 239(1). (Apr. 2006),209-16.
Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.
Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.
Liliane Ramus et al., "Assessing selection methods in the cotnext of multi-atlas based segmentation," Biomedical Imaging: From Nano to Macro, 2010, IEEE International Symposium, Apr. 14, 2010, pp. 1321-1324.

(56) References Cited

OTHER PUBLICATIONS

Olivier Commowick et al., "Using Frankenstein's Creature Paradigm to Build a Patient Specific Atlas," Sep. 20, 2009, Medical Image Computing and Computer-Assisted Intervention, pp. 993-1000.

Lotjonen J.M.P. et al., "Fast and robust multi-atlas segmentation of brain magnetic resonance images," NeuroImage, Academic Press, vol. 49, No. 3, Feb. 1, 2010, pp. 2352-2365.

McIntyre, C. C., et al., "How does deep brain stimulation work? Present understanding and future questions.", J Clin Neurophysiol. 21 (1 ). (Jan.-Feb. 2004 ),40-50.

Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.

Plaha, P. , et al., "Stimulation of the caudal zona incerta is superior to stimulation of the subthalamic nucleus in improving contralateral parkinsonism.", Brain 129{Pt 7) (Jul. 2006), 1732-4 7.

Rattay, F, "Analysis of models for external stimulation of axons", IEEE Trans. Biomed. Eng. vol. 33 (1986), 974-977.

Rattay, F., "Analysis of the electrical excitation of CNS neurons", IEEE Transactions on Biomedical Engineering 45(6). (Jun. 1998),766-772.

Rose, T. L., et al., "Electrical stimulation with Pt electrodes. VIII. Electrochemically safe charge injection limits with 0.2ms pulses [neuronal application]", IEEE Transactions on Biomedical Engineering, 37(11 }, (Nov. 1990), 1118-1120.

Rubinstein, J. T., et al., "Signal coding in cochlear implants: exploiting stochastic effects of electrical stimulation", Ann Otol Rhinol Laryngol Suppl.. 191, (Sep. 2003), 14-9.

Schwan, H.P., et al., "The conductivity of living tissues.", Ann NY Acad Sci., 65(6). (Aug. 1957),1007-13.

Taylor, R. S., et al., "Spinal cord stimulation for chronic back and leg pain and failed back surgery syndrome: a systematic review and analysis of prognostic factors", Spine 30(1 ). (Jan. 1, 2005), 152-60.

Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.

Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.

Geddes, L. A., et al., "The specific resistance of biological material—a compendium of data for the biomedical engineer and physiologist.", Med Biol Ena. 5(3). (May 1967),271-93.

Gimsa, J., et al., "Choosing electrodes for deep brain stimulation experiments—electrochemical considerations.", J Neurosci Methods, 142(2), (Mar. 30, 2005),251-65.

Vidailhet, M. , et al., "Bilateral deep-brain stimulation of the globus pallidus in primary generalized dystonia", N Engl J Med. 352(5) (Feb. 3, 2005),459-67.

Izad, Oliver, "Computationally Efficient Method in Predicating Axonal Excitation," Dissertation for Master Degree, Department of Biomedical Engineering, Case Western Reserve University, May 2009.

Jaccard, Paul, "Elude comparative de la distribution florale dans une portion odes Aples et des Jura," Bulletin de la Societe Vaudoise des Sciences Naturelles (1901), 37:547-579.

Dice, Lee R., "Measures of the Amount of Ecologic Association Between Species," Ecology 26(3) (1945): 297-302. doi: 10.2307/1932409, http://jstor.org/stable/1932409.

Rand, WM., "Objective criteria for the evaluation of clustering methods," Journal of the American Statistical Association (American Statistical Association) 66 (336) (1971 ): 846-850, doi:10.2307/2284239, http://jstor.org/stable/2284239.

Hubert, Lawrence et al., "Comparing partitions," Journal of Classification 2(1) (1985): 193-218, doi:10.1007/BF01908075.

Cover, T.M. et al., "Elements of information theory," (1991) John Wiley & Sons, New York, NY.

Meila, Marina, "Comparing Clusterings by the Variation of Information," Learning Theory and Kernel Machines (2003): 173-187.

Viola, P., et al., "Alignment by maximization of mutual information", International Journal of Com outer Vision 24(2). ( 1997), 137-154.

Butson et al. "StimExplorer: Deep Brain Stimulation Parameter Selection Software System," Acta Neurochirugica, Jan. 1, 2007, vol. 97, No. 2, pp. 569-574.

Butson et al. "Role of Electrode Design on the Volume of Tissue Activated During Deep Brain Stimulation," Journal of Neural Engineering, Mar. 1, 2006, vol. 3, No. 1, pp. 1-8.

Volkmann et al., Indroduction to the Programming of Deep Brain Stimulators, Movement Disorders, vol. 17, Suppl. 3, pp. S181-S187 (2002).

Miocinovic et al. "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.

Schmidt et al. "Sketching and Composing Widgets for 3D Manipulation," Eurographics, Apr. 2008, vol. 27, No. 2, pp. 301-310.

Volkmann, J. , et al., "Basic algorithms for the programming of deep brain stimulation in Parkinson's disease", Mov Disord., 21 Suppl 14. (Jun. 2006),S284-9.

Walter, B. L., et al., "Surgical treatment for Parkinson's disease", Lancet Neural. 3(12). (Dec. 2004),719-28.

Wei, X. F., et al., "Current density distributions, field distributions and impedance analysis of segmented deep brain stimulation electrodes", J Neural Eng .. 2(4). (Dec. 2005), 139-47.

Zonenshayn, M. , et al., "Location of the active contact within the subthalamic nucleus (STN) in the treatment of diopathic Parkinson's disease.", Surg Neurol., 62(3) (Sep. 2004),216-25.

Da Silva et al (A primer on diffusion tensor imaging of anatomical substructures. Neurosurg Focus 15(1): p. 1-4, Article 4, 2003.).

Micheli-Tzanakou, E., et al., "Computational Intelligence for target assesment in Parkinson's disease", Proceedings of SPIE vol. 4479. Applications and Science of Neural Networks, Fuzzy Systems, and Evolutionary Computation IV,(2001),54-69.

Grill, W. M., "Stimulus waveforms for selective neural stimulation", IEEE Engineering in Medicine and Biology Magazine, 14(4}, (Jul.-Aug. 1995), 375-385.

Miocinovic, S., et al., "Sensitivity of temporal excitation properties to the neuronal element activated by extracellular stimulation", J Neurosci Methods. 132(1). (Jan. 15, 2004), 91-9.

Hunka, K. et al., Nursing Time to Program and Assess Deep Brain Stimulators in Movement Disorder Patients, J. Neursci Nurs., 37: 204-10 (Aug. 2005).

Moss, J. , et al., "Electron microscopy of tissue adherent to explanted electrodes in dystonia and Parkinson's disease", Brain, 127{Pt 12). (Dec. 2004 ),2755-63.

Montgomery, E. B., et al., "Mechanisms of deep brain stimulation and future technical developments.", Neurol Res. 22(3). (Apr. 2000),259-66.

Merrill, D. R., et al., "Electrical stimulation of excitable tissue: design of efficacious and safe protocols", J Neurosci Methods. 141(2), (Feb. 15, 2005), 171-98.

Fisekovic et al., "New Controller for Functional Electrical Stimulation Systems", Med. Eng. Phys. 2001; 23:391-399.

Butson et al., "Tissue and Electrode Capacitance Reduce Neural Activation Volumes During Deep Brain Stimulation", Clinical Neurophysiology, 116:2490-2500, Oct. 2005.

Butson et al., "Sources and Effects of Electrode Impedance During Deep Brain Stimulation", Clinical Neurophysiology, 117:44 7-454, Dec. 2005.

D'Haese et al., "Computer-Aided Placement of Deep Brain Stimulators: From Planning to Intraoperative Guidance", IEEE Transaction on Medical Imaging, 24:1469-1478, Nov. 2005.

Gross et al., "Electrophysiological Mapping for the Implantation of Deep Brain Stimulators for Parkinson's Disease and Tremor", Movement Disorders, 21 :S259-S283, Jun. 2006.

Halpern et al., "Brain Shift During Deep Brain Stimulation Surgery for Parkinson's Disease", Stereotact Funct. Neurosurg., 86:37-43, published online Sep. 2007.

(56) References Cited

OTHER PUBLICATIONS

Herzog et al., "Most Effective Stimulation Site in Subthalamic Deep Brain Stimulation for Parkinson's Disease", Movement Disorders, 19:1050-1099, published on line Mar. 2004.
Jeon et al., A Feasibility Study of Optical Coherence Tomography for Guiding Deep Brain Probes, Journal of Neuroscience Methods, 154:96-101, Jun. 2006.
Khan et al., "Assessment of Brain Shift Related to Deep Brain Stimulation Surgery", Sterreotact Funct. Neurosurg., 86:44-53, published online Sep. 2007.
Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.
Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.
Machado et al., "Deep Brain Stimulation for Parkinson's Disease: Surgical Technique and Perioperative Management", Movement Disorders, 21 :S247-S258, Jun. 2006.
Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.
Moran et al., "Real-Time Refinment of Subthalamic Nucleous Targeting Using Bayesian Decision-Making on the Root Mean Square Measure", Movement Disorders, 21: 1425-1431, published online Jun. 2006.
Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.
Winkler et al., The First Evaluation of Brain Shift During Functional Neurosurgery by Deformation Field Analysis, J. Neural. Neurosurg. Psychiatry, 76:1161-1163, Aug. 2005.
Yelnik et al., "A Three-Dimensional, Histological and Deformable Atlas of the Human Basal J Ganglia. I. Atlas Construction Based on Immunohistochemical and MRI Data", NeuroImage, 34:618,-638,Jan. 2007.
Ward, H. E., et al., "Update on deep brain stimulation for neuropsychiatric disorders," Neurobiol Dis 38 (3) (2010), pp. 346-353.
Alberts et al. "Bilateral subthalamic stimulation impairs cognitive-motor performance in Parkinson's disease patients." Brain (2008), 131, 3348-3360, Abstract.
Butson, Christopher R., et al., "Sources and effects of electrode impedance during deep brain stimulation", Clinical Neurophysiology. vol. 117.(2006),447-454.
An, et al., "Prefrontal cortical projections to longitudinal columns in the midbrain periaqueductal gray in macaque monkeys," J Comp Neural 401 (4) (1998), pp. 455-479.
Bulson, C. R., et al., "Tissue and electrode capacitance reduce neural activation volumes during deep brain stimulation," Clinical Neurophysiology, vol. 116 (2005), pp. 2490-2500.
Carmichael, S. T., et al., "Connectional networks within the orbital and medial prefrontal cortex of macaque monkeys," J Comp Neural 371 (2) (1996), pp. 179-207.
Croxson, et al., "Quantitative investigation of connections of the prefrontal cortex in the human and macaque using probabilistic diffusion tractography," J Neurosci 25 (39) (2005), pp. 8854-8866.
Frankemolle, et al., "Reversing cognitive-motor impairments in Parkinson's disease patients using a computational modelling approach to deep brain stimulation programming," Brain 133 (2010), pp. 746-761.
Freedman, et al., "Subcortical projections of area 25 (subgenual cortex) of the macaque monkey," J Comp Neurol 421 (2) (2000), pp. 172-188.

Giacobbe, et al., "Treatment resistant depression as a failure of brain homeostatic mechanisms: implications for deep brain stimulation," Exp Neural 219 (1) (2009), pp. 44-52.
Goodman, et al., "Deep brain stimulation for intractable obsessive compulsive disorder: pilot study using a blinded, staggered-onset design," Biol Psychiatry 67 (6) (2010), pp. 535-542.
Greenberg, et al., "Deep brain stimulation of the ventral internal capsule/ventral striatum for obsessive-compulsive disorder: worldwide experience," Mol Psychiatry 15 (1) (2010), pp. 64-79.
Greenberg et al., "Three-year outcomes in deep brain stimulation for highly resistant obsessive-compulsive disorder," Neuropsychopharmacology 31 (11) (2006), pp. 2384-2393.
Gutman, et al., "A tractography analysis of two deep brain stimulation white matter targets for depression," Biol Psychiatry 65 (4) (2009), pp. 276-282.
Haber, et al., "Reward-related cortical inputs define a large striatal region in primates that interface with associative cortical connections, providing a substrate for incentive-based learning," J Neurosci 26 (32) (2006), pp. 8368-8376.
Haber, et al., "Cognitive and limbic circuits that are affected by deep brain stimulation," Front Biosci 14 (2009), pp. 1823-1834.
Hines, M. L., et al., "The Neuron simulation environment," Neural Comput., 9(6) (Aug. 15, 1997), pp. 1179-1209.
Hua, et al., "Tract probability maps in stereotaxic spaces: analyses of white matter anatomy and tract-specific quantification," Neuroimage 39 (1) (2008), pp. 336-347.
Johansen-Berg, et al., "Anatomical connectivity of the subgenual cingulate region targeted with deep brain stimulation for treatment-resistant depression," Cereb Cortex 18 (6) (2008), pp. 1374-1383.
Kopell, et al., "Deep brain stimulation for psychiatric disorders," J Clin Neurophysiol 21 (1) (2004), pp. 51-67.
Lozano, et al., "Subcallosal cingulate gyrus deep brain stimulation for treatment-resistant depression," Biol Psychiatry 64 (6) (2008), pp. 461-467.
Lujan, et al., "Tracking the mechanisms of deep brain stimulation for neuropsychiatric disorders," Front Biosci 13 (2008), pp. 5892-5904.
Lujan, J.L. et al., "Automated 3-Dimensional Brain Atlas Fitting to Microelectrode Recordings from Deep Brain Stimulation Surgeries," Stereotact. Fune!. Neurosurg. 87(2009), pp. 229-240.
Machado. et al., "Functional topography of the ventral striatum and anterior limb of the internal capsule determined by electrical stimulation of awake patients," Clin Neurophysiol 120 (11) (2009), pp. 1941-1948.
Malone, et al., "Deep brain stimulation of the ventral capsule/ventral striatum for treatment-resistant depression," Biol Psychiatry 65 (4) (2009), pp. 267-275.
Mayberg, H. S., et al., "Deep brain stimulation for treatment-resistant depression," Neuron, 45(5) (Mar. 3, 2005), pp. 651-660.
Mayberg, H. S., et al., "Limbic-cortical dysregulation: a proposed model of depression," J Neuropsychiatry Clin Neurosci. 9 (3) (1997), pp. 471-481.
McIntyre, C. C., et al., "Network perspectives on the mechanisms of deep brain stimulation," Neurobiol Dis 38 (3) (2010), pp. 329-337.
Miocinovic, S., et al., "Experimental and theoretical characterization of the voltage distribution generated by deep brain stimulation," Exp Neurol 216 (i) (2009), pp. 166-176.
Nuttin, et al., "Electrical stimulation in anterior limbs of internal capsules in patients with obsessive-compulsive disorder," Lancet 354 (9189) (1999), p. 1526.
Saxena, et al., "Cerebral glucose metabolism in obsessive-compulsive hoarding," Am J Psychiatry. 161 (6) (2004), pp. 1038-1048.
Viola, et al., "Importance-driven focus of attention," IEEE Trans Vis Comput Graph 12 (5) (2006), pp. 933-940.
Wakana, S., et al., "Reproducibility of quantitative tractography methods applied to cerebral white matter," Neuroimage 36 (3) (2007), pp. 630-644.
Mayr et al., "Basic Design and Construction of the Vienna FES Implants: Existing Solutions and Prospects for New Generations of Implants", Medical Engineering & Physics, 2001; 23:53-60.

(56) References Cited

OTHER PUBLICATIONS

Zhang, Y., et al., "Atlas-guided tract reconstruction for automated and comprehensive examination of the white matter anatomy," Neuroimage 52(4) (2010), pp. 1289-1301.

"BioPSE" The Biomedical Problem Solving Environment, htt12://www.sci.utah.edu/cibc/software/index.html, MCRR Center for Integrative Biomedical Computing,(2004).

Andrews, R. J., "Neuroprotection trek—the next generation: neuromodulation I. Techniques—deep brain stimulation, vagus nerve stimulation, and transcranial magnetic stimulation.", Ann NY Acad Sci. 993. (May 2003),1-13.

Carnevale, N.T. et al., "The Neuron Book," Cambridge, UK: Cambridge University Press (2006), 480 pages.

Chaturvedi: "Development of Accurate Computational Models for Patient-Specific Deep Brain Stimulation," Electronic Thesis or Dissertation, Jan. 2012, 162 pages.

Chaturvedi, A. et al.: "Patient-specific models of deep brain stimulation: Influence of field model complexity on neural activation predictions." Brain Stimulation, Elsevier, Amsterdam, NL, vol. 3, No. 2 Apr. 2010, pp. 65-77.

Frankemolle, et al., "Reversing cognitive-motor impairments in Parkinson's disease patients using a computational modeling approach to deep brain stimulation programming," Brian 133 (2010), pp. 746-761.

McIntyre, C.C., et al., "Modeling the excitablitity of mammalian nerve fibers: influence of afterpotentials on the recovery cycle," J Neurophysiol, 87(2) (Feb. 2002), pp. 995-1006.

Peterson, et al., "Predicting myelinated axon activation using spatial characteristics of the extracellular field," Journal of Neural Engineering, 8 (2011), 12 pages.

Warman, et al., "Modeling the Effects of Electric Fields on nerver Fibers; Dermination of Excitation Thresholds," IEEE Transactions on Biomedical Engineering, vol. 39, No. 12 (Dec. 1992), pp. 1244-1254.

Wesselink, et al., "Analysis of Current Density and Related Parameters in Spinal Cord Stimulation," IEEE Transactions on Rehabilitation Engineering, vol. 6, No. 2 Jun. 1998, pp. 200-207.

Andrews, R. J., "Neuroprotection trek—the next generation: neuromodulation II. Applications—epilepsy, nerve regeneration, neurotrophins.", Ann NY Acad Sci. 993 (May 2003), 14-24.

Astrom, M. , et al., "The effect of cystic cavities on deep brain stimulation in the basal ganglia: a simulation-based study", J Neural Eng., 3(2), (Jun. 2006).132-8.

Bazin et al., "Free Software Tools for Atlas-based Volumetric Neuroimage Analysis", Proc. SPIE 5747, Medical Imaging 2005: Image Processing, 1824 May 5, 2005.

Back, C. , et al., "Postoperative Monitoring of the Electrical Properties of Tissue and Electrodes in Deep Brain Stimulation", Neuromodulation, 6(4), (Oct. 2003 ),248-253.

Baker, K. B., et al., "Evaluation of specific absorption rate as a dosimeter of MRI-related implant heating", J Magn Reson Imaging., 20(2), (Aug. 2004),315-20.

Brown, J. "Motor Cortex Stimulation," Neurosurgical Focus ( Sep. 15, 2001) 11(3):E5.

Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.

Cesselin, F. "Opioid and anti-opioid peptides," Fundamental and Clinical Pharmacology (1995) 9(5): 409-33 (Abstract only).

Rezai et al., "Deep Brain Stimulation for Chronic Pain" Surgical Management of Pain, Chapter 44 pp. 565-576 (2002).

Xu, Md., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102(5) pp. 363-367 May 1993.

Bedard, C. , et al., "Modeling extracellular field potentials and the frequency-filtering properties of extracellular space", Biophys J .. 86(3). (Mar. 2004),1829-42.

Benabid, A. L., et al., "Future prospects of brain stimulation", Neurol Res.,22(3), (Apr. 2000),237-46.

Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977),440-443.

Butson, Christopher R., et al., "Deep Brain Stimulation of the Subthalamic Nucleus: Model-Based Analysis of the Effects of Electrode Capacitance on the Volume of Activation", Proceedings of the 2nd International IEEE EMBS, (Mar. 16-19, 2005),196-197.

Mcintyre, Cameron C., et al., "Cellular effects of deep brain stimulation: model-based analysis of activation and inhibition," J Neurophysiol, 91(4) (Apr. 2004), pp. 1457-1469.

Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006. EMBS' 06 28th Annual International Conference of the IEEE, IEEE, Piscataway, NJ USA, Aug. 30, 2006.

Butson, Christopher et al., "Predicting the Effects of Deep Brain Stimulation with Diffusion Tensor Based Electric Field Models" Jan. 1, 2001, Medical Image Computing and Computer-Assisted Intervention—Mic CAI 2006 Lecture Notes in Computer Science; LNCS, Springer, Berlin, DE.

Butson, C. R., et al., "Deep brainstimulation interactive visualization system", Society for Neuroscience vol. 898.7 (2005).

Hodaie, M., et al., "Chronic anterior thalamus stimulation for intractable epilepsy," Epilepsia, 43(6) (Jun. 2002), pp. 603-608.

Hoekema, R., et al., "Multigrid solution of the potential field in modeling electrical nerve stimulation," Comput Biomed Res., 31(5) (Oct. 1998), pp. 348-362.

Holsheimer, J., et al., "Identification of the target neuronal elements in electrical deep brain stimulation," Eur J Neurosci., 12(12) (Dec. 2000), pp. 4573-4577.

Jezernik, S., et al., "Neural network classification of nerve activity recorded in a mixed nerve," Neurol Res., 23(5) (Jul. 2001), pp. 429-434.

Jones, DK., et al., "Optimal strategies for measuring diffusion in anisotropic systems by magnetic resonance imaging," Magn. Reson. Med., 42(3) (Sep. 1999), pp. 515-525.

Krack, P., et al., "Postoperative management of subthalamic nucleus stimulation for Parkinson's disease," Mov. Disord., vol. 17(suppl 3) (2002), pp. 188-197.

Le Bihan, D., et al., "Diffusion tensor imaging: concepts and applications," J Magn Reson Imaging, 13(4) (Apr. 2001), pp. 534-546.

Lee, D. C., et al., "Extracellular electrical stimulation of central neurons: quantitative studies," In: Handbook of neuroprosthetic methods, WE Finn and PG Lopresti (eds) CRC Press (2003), pp. 95-125.

Levy, AL., et al., "An Internet-connected, patient-specific, deformable brain atlas integrated into a surgical navigation system," J Digit Imaging, 10(3 Suppl 1) (Aug. 1997), pp. 231-237.

Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.

Mcintyre, C. C., et al., "Extracellular stimulation of central neurons: influence of stimulus waveform and frequency on neuronal output," J. Neurophysiol., 88(4), (Oct. 2002), pp. 1592-1604.

Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.

Mcintyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cal. No. 02CH37392) IEEEPiscataway, NJ (2002), pp. 2047-2048.

Mcintyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001), pp. 806-809.

(56) References Cited

OTHER PUBLICATIONS

Mcintyre, C. C., et al., Model-based design of stimulus waveforms for selective microstimulation in the central nervous system,, Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999), p. 384.

Mcintyre, Cameron C., et al., "Modeling the excitability of mammalian nerve fibers: influence of afterpotentials on the recovery cycle," J Neurophysiol, 87(2) (Feb. 2002), pp. 995-1006.

Mcintyre, Cameron C., et al., "Selective microstimulation of central nervous system neurons," Annals of biomedical engineering, 28(3) (Mar. 2000), pp. 219-233.

Mcintyre, C. C., et al., "Sensitivity analysis of a model of mammalian neural membrane," Biol Cybern., 79(1) (Jul. 1998), pp. 29-37.

Mcintyre, Cameron C., et al., "Uncovering the mechanism(s) of action of deep brain stimulation: activation, inhibition, or both," Clin Neurophysiol, 115(6) (Jun. 2004), pp. 1239-1248.

Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.

Mouine et al. "Multi-Strategy and Multi-Algorithm Cochlear Prostheses", Biomed. Sci. Instrument, 2000; 36:233-238.

Mitra PP, Pesaran B. Analysis of dynamic brain imaging data. Biophys J. Feb. 1999;76(2):691-708. doi: 10.1016/S0006-3495(99)77236-X. PMID: 9929474; PMCID: PMC 1300074.

Hammer N, Glätzner J, Feja C, Kühne C, Meixensberger J, et al. (2015) Human Vagus Nerve Branching in the Cervical Region. PLOS ONE 10(2): e0118006. Published: Feb. 13, 2015. https://doi.org/10.1371/journal.pone.0118006.

Trost M, Su S, Su P, Yen RF, Tseng HM, Barnes A, Ma Y, Eidelberg D. Network modulation by the subthalamic nucleus in the treatment of Parkinson's disease. Neuroimage. May 15, 2006;31(1):301-7. doi: 10.1016/j. neuroimage.2005.12.024. Epub Feb. 8, 2006.

Alo, K. M., et al., "New trends in neuromodulation for the management of neuropathic pain," Neurosurgery, 50(4), (Apr. 2002), pp. 690-703, discussion pp. 703-704.

Ashby, P., et al., "Neurophysiological effects of stimulation through electrodes in the human subthalamic nucleus," Brain, 122 (PI 10), (Oct. 1999), pp. 1919-1931.

Baker, K. B., et al., "Subthalamic nucleus deep brain stimulus evoked potentials: Physiological and therapeutic Implications," Movement Disorders, 17(5), (Sep./Oct. 2002), pp. 969-983.

Bammer, R, et al., "Diffusion tensor imaging using single-shot SENSE-EPI", Magn Reson Med., 48(1 ), (Jul. 2002), pp. 128-136.

Basser, P J., et al., "MR diffusion tensor spectroscopy and imaging," Biophys J., 66(1 ), (Jan. 1994), pp. 259-267.

Basser, P J., et al., "New currents in electrical stimulation of excitable tissues," Annu Rev Biomed Eng., 2, (2000), pp. 377-397.

Benabid, AL., et al., "Chronic electrical stimulation of the ventralis intermedius nucleus of the thalamus as a treatment of movement disorders," J. Neurosurg., 84(2), (Feb. 1996), pp. 203-214.

Benabid, AL., et al., "Combined (Ihalamotoy and stimulation) stereotactic surgery of the VIM thalamic nucleus for bilateral Parkinson disease," Appl Neurophysiol, vol. 50, (1987), pp. 344-346.

Benabid, A L., et al., "Long-term suppression of tremor by chronic stimulation of the ventral intermediate thalamic nucleus," Lancet, 337 (8738), (Feb. 16, 1991 ), pp. 403-406.

Butson, C. R., et al., "Predicting the effects of deep brain stimulation with diffusion tensor based electric field models," Medical Image Computing and Computer-Assisted Intervention—Mic Cai 2006, Lecture Notes in Computer Science (LNCS), vol. 4191, pp. 429-437, LNCS, Springer, Berlin, DE.

Christensen, Gary E., et al., "Volumetric transformation of brain anatomy," IEEE Transactions on Medical Imaging, 16 (6), (Dec. 1997), pp. 864-877.

Cooper, S , et al., "Differential effects of thalamic stimulation parameters on tremor and paresthesias in essential tremor," Movement Disorders, 17(Supp. 5), (2002), p. S193.

Coubes, P, et al., "Treatment of DYT1-generalised dystonia by stimulation of the internal globus pallidus," Lancet, 355(9222), (Jun. 24, 2000), pp. 2220-2221.

Dasilva, A.F. M., et al., "A Primer Diffusion Tensor Imaging of Anatomical Substructures," Neurosurg. Focus; 15(1) (Jul. 2003), pp. 1-4.

Dawant, B. M., et al., "Compuerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany(2003), pp. 142-150.

Finnis, K. W., et al., "3-D functional atalas of subcortical structures for image guided stereotactic neurosurgery," Neuroimage, vol. 9, No. 6, Iss. 2 (1999), p. S206.

Finnis, K. W., et al., "3D Functional Database of Subcorticol Structures for Surgical Guidance in Image Guided Stereotactic Neurosurgery," Medical Image Computing and Computer-Assisted Intervention—MICCAI'99, Second International Conference. Cambridge, UK, Sep. 19-22, 1999, Proceedings (1999), pp. 758-767.

Finnis, K. W., et al., "A 3-Dimensional Database of Deep Brain Functional Anatomy, and Its Application to Image-Guided Neurosurgery," Proceedings of the Third International Conference on Medical Image Computing and Computer-Assisted Intervention. Lecture Notes in Computer Science; vol. 1935 (2000), pp. 1-8.

Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.

Finnis, K. W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention—Part 11, Lecture Notes in Computer Science; vol. 2489 (2002), pp. 69-76.

Finnis, K. W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 2002), pp. 184-195.

Finnis, Krik W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.

Gabriels, L , et al., "Deep brain stimulation for treatment-refractory obsessive-compulsive disorder: psychopathological and neuropsychological outcome in three cases," Acta Psychiatr Scand., 107(4) (2003), pp. 275-282.

Gabriels, LA., et al., "Long-term electrical capsular stimulation in patients with obsessive-compulsive disorder," Neurosurgery, 52(6) (Jun. 2003), pp. 1263-1276.

Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.

Goodall, E. V., et al., "Position-selective activation of peripheral nerve fibers with a cuff electrode," IEEE Transactions on Biomedical Engineering, 43(8) (Aug. 1996), pp. 851-856.

Goodall, E. V., "Simulation of activation and propagation delay during tripolar neural stimulation," Proceedings of the 15th Annual International Conference of the IEEE Engineering in Medicine and Biology Society (1993), pp. 1203-1204.

Grill, WM., "Modeling the effects of electric fields on nerve fibers: influence of tissue electrical properties," IEEE Transactions on Biomedical Engineering, 46(8) (1999), pp. 918-928.

Grill, W. M., et al., "Neural and connective tissue response to long-term implantation of multiple contact nerve cuff electrodes," J Biomed Mater Res., 50(2) (May 2000), pp. 215-226.

(56) References Cited

OTHER PUBLICATIONS

Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.

Grill, W. M., et al., "Non-invasive measurement of the input-output properties of peripheral nerve stimulating electrodes," Journal of Neuroscience Methods, 65(1) (Mar. 1996), pp. 43-50.

Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.

Grill, W. M., "Spatially selective activation of peripheral nerve for neuroprosthetic applications," Ph.D. Case Western Reserve University, (1995), pp. 245 pages.

Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.

Grill, W. M., "Stimulus waveforms for selective neural stimulation," IEEE Engineering in Medicine and Biology Magazine, 14(4) (Jul.-Aug. 1995), pp. 375-385.

Grill, W. M., et al., "Temporal stability of nerve cuff electrode recruitment properties," IEEE 17th Annual Conference Engineering in Medicine and Biology Society, vol. 2 (1995), pp. 1089-1090.

Gross, RE., et al., "Advances in neurostimulation for movement disorders," Neurol Res., 22(3) (Apr. 2000), pp. 247-258.

Guridi et al., "The subthalamic nucleus, hemiballismus and Parkinson's disease: reappraisal of a neurological dogma," Brain, vol. 124, 2001, pp. 5-19.

Haberler, C, et al., "No tissue damage by chronic deep brain stimulation in Parkinson's disease," Ann Neurol., 48(3) (Sep. 2000), pp. 372-376.

Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.

Hanekom, "Modelling encapsulation tissue around cochlear implant electrodes," Med. Biol. Eng. Comput. vol. 43 (2005), pp. 47-55.

Haueisen, J , et al., "The influence of brain tissue anisotropy on human EEG and MEG," Neuroimage, 15(1) (Jan. 2002), pp. 159-166.

D'Haese et al. Medical Image Computing and Computer-Assisted Intervention—MICCAI 2005 Lecture Notes in Computer Science, 2005, vol. 3750, 2005, 427-434.

Rohde et al. IEEE Transactions on Medical Imaging, vol. 22 No. 11, 2003 p. 1470-1479.

Dawant et al., Biomedical Image Registration. Lecture Notes in Computer Science, 2003, vol. 2717, 2003, 142-150.

Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.

Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.

Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.

Andrade-Souza, "Comparison of Three Methods of Targeting the Subthalamic Nucleus for Chronic Stimulation in Parkinson's Disease", Neurosurgery, 56:360-368, Apr. 2005.

Anheim et al., "Improvement in Parkinson Disease by Subthalamic Nucleus Stimulation Based on Electrode Placement", Arch Neural., 65:612-616, May 2008.

\* cited by examiner

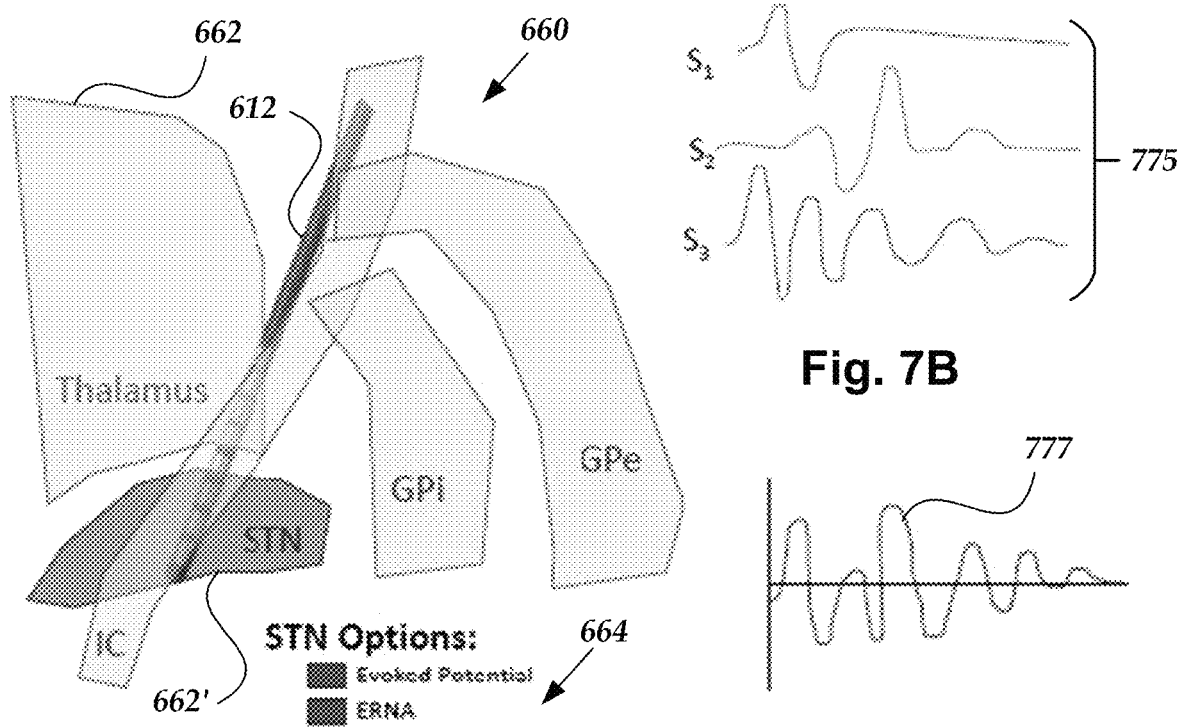
Fig. 7B
Fig. 6
Fig. 7C
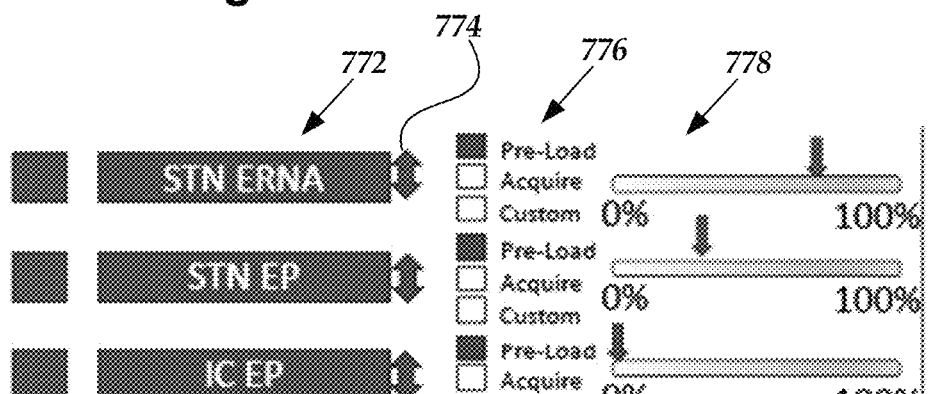
Fig. 7A
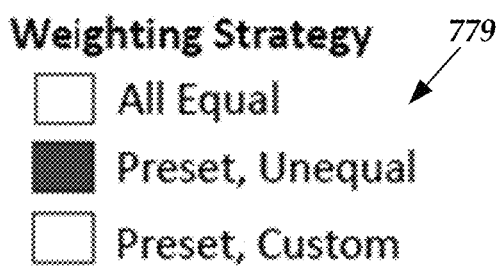
Fig. 7D

METHODS AND SYSTEMS FOR ESTIMATING NEURAL ACTIVATION BY STIMULATION USING A STIMULATION SYSTEM

CROSS-REFERENCE TO RELATED APPLICATIONS

This application claims the benefit under 35 U.S.C. § 119(e) of U.S. Provisional Patent Application Ser. No. 63/210,799, filed Jun. 15, 2021, which is incorporated herein by reference.

FIELD

The present disclosure is directed to the area of implantable electrical stimulation systems and methods of making and using the systems. The present disclosure is also directed to methods and systems for estimating neural activation by stimulation using the implantable electrical stimulation system.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Deep brain stimulation can be used to treat a variety of diseases and disorders.

Stimulators have been developed to provide therapy for a variety of treatments. A stimulator can include a control module (with a pulse generator) and one or more stimulator electrodes. The one or more stimulator electrodes can be disposed along one or more leads, or along the control module, or both. The stimulator electrodes are in contact with or near the nerves, muscles, or other tissue to be stimulated. The pulse generator in the control module generates electrical pulses that are delivered by the electrodes to body tissue.

BRIEF SUMMARY

One aspect is a method for estimating neural activation arising from stimulation by a stimulation system. The method includes identifying a plurality of different neural elements stimulated by the stimulation; obtaining a neural response signal resulting from the stimulation by the stimulation system; and decomposing the neural response signal to estimate neural activation of each of the different neural elements.

In at least some aspects, the method further includes, for each of the different neural elements, providing at least one template signal for the neural element, wherein decomposing the neural response signal includes decomposing the neural response signal using the template signals. In at least some aspects, decomposing the neural response signal using the template signals includes determining weights for each of the template signals as portions of the neural response signal.

In at least some aspects, decomposing the neural response signal includes decomposing the neural response signal in a frequency domain. In at least some aspects, the method further includes transforming the neural response signal into the frequency domain. In at least some aspects, the method further includes determining initial weights for each of the template signals using one or more frequency components in the template signals. In at least some aspects, the method further includes combining the template signals using the weights to generate a composite neural signal. In at least some aspects, the method further includes determining a difference between the neural response signal and the composite neural signal. In at least some aspects, the method further includes determining whether the difference exceeds a predetermined threshold difference and, when so, adjusting the weights.

In at least some aspects, decomposing the neural response signal includes decomposing the neural response signal in a time domain. In at least some aspects, the method further includes combining the template signals using the weights to generate a composite neural signal. In at least some aspects, determining a difference between the neural response signal and the composite neural signal. In at least some aspects, the method further includes determining whether the difference exceeds a predetermined threshold difference and, when so, adjusting the weights. In at least some aspects, the method further includes filtering the neural response signal.

Another aspect is a system for estimating neural activation arising from stimulation by a stimulation system. The system includes at least one processor configured to perform actions, including: receiving an identification of a plurality of different neural elements stimulated by the stimulation; receiving a neural response signal resulting from the stimulation by the stimulation system; and decomposing the neural response signal to estimate neural activation of each of the different neural elements. The actions further include any of the methods described above.

In at least some aspects, the actions further include, for each of the different neural elements, obtaining at least one template signal for the neural element, wherein decomposing the neural response signal includes decomposing the neural response signal using the template signals. In at least some aspects, the system further includes a display and at least one input device coupled to the at least one processor, wherein the actions further include, for each of the different neural elements, receive a selection of a type of signal to be used for the template signal.

In at least some aspects, the system further includes a display and at least one input device coupled to the at least one processor, wherein receiving the identification includes displaying a representation of one or more anatomical regions; receiving a selection by the user of one of the anatomical regions; and identifying one or more of the different neural elements based on the selection of the one of the anatomical regions.

A further aspect is a non-transitory computer-readable medium having processor-executable instructions for estimating neural activation arising from stimulation by a stimulation system, the processor-executable instructions when installed onto a device enable the device to perform actions, the actions including: receiving an identification of a plurality of different neural elements stimulated by the stimulation; receiving a neural response signal resulting from the stimulation by the stimulation system; and decomposing the neural response signal to estimate neural activation of each of the different neural elements. The actions further include any of the methods described above.

In at least some aspects, the actions further include, for each of the different neural elements, obtaining at least one template signal for the neural element, wherein decomposing the neural response signal includes decomposing the neural response signal using the template signals.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 6 is a schematic representation of one embodiment of a user interface for selection of anatomical regions;

FIG. 7A is a schematic representation of one embodiment of a user interface for selecting which neural signals to use for the neural elements;

FIG. 7B is a schematic representation of one embodiment of three template signals for neural elements;

FIG. 7C is a schematic representation of one embodiment of a composite signal using a weighted combination of the three template signals of FIG. 7B;

FIG. 7D is a schematic representation of one embodiment of a user interface for selecting a weighting strategy;

DETAILED DESCRIPTION

The present disclosure is directed to the area of implantable electrical stimulation systems and methods of making and using the systems. The present disclosure is also directed to methods and systems for estimating neural activation by stimulation using the implantable electrical stimulation system.

Suitable implantable electrical stimulation systems include, but are not limited to, a least one lead with one or more electrodes disposed on a distal portion of the lead and one or more terminals disposed on one or more proximal portions of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Application Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated herein by reference. In the discussion below, a percutaneous lead will be exemplified, but it will be understood that the methods and systems described herein are also applicable to paddle leads and other leads.

A percutaneous lead for electrical stimulation (for example, deep brain, spinal cord, or peripheral nerve stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes. For illustrative purposes, the systems and leads are described herein relative to use for deep brain stimulation, but it will be understood that any of the leads can be used for applications other than deep brain stimulation, including spinal cord stimulation, peripheral nerve stimulation, dorsal root ganglion stimulation, sacral nerve stimulation, or stimulation of other nerves, muscles, and tissues.

Figure 1:
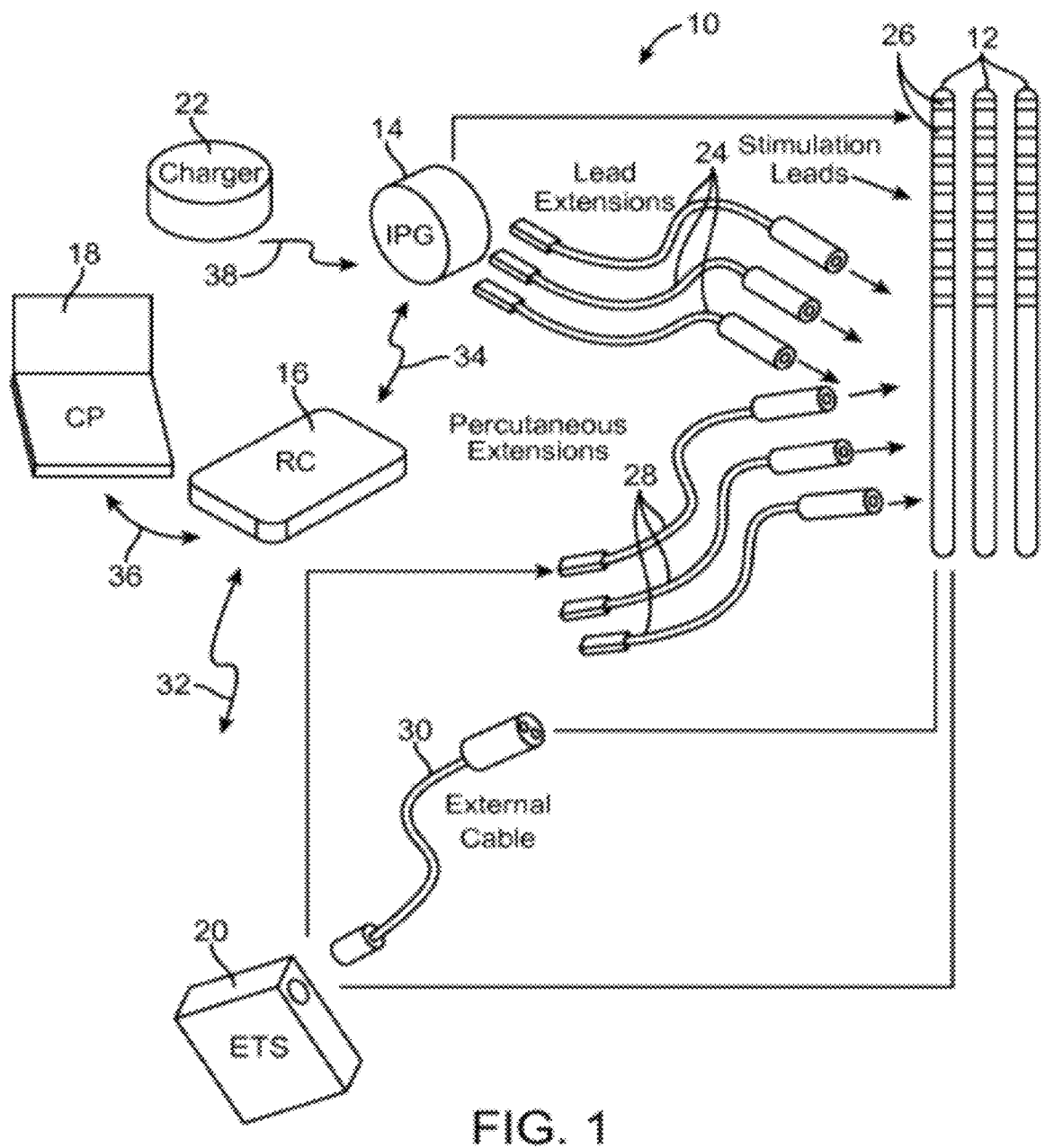
FIG. 1 is a schematic view of one embodiment of an electrical stimulation system.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22. The IPG and ETS are examples of control modules for the electrical stimulation system.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity or at any other suitable site. The implantable pulse generator can have multiple stimulation channels which may be independently programmable to control the magnitude of the current stimulus from each channel. In some embodiments, the implantable pulse generator can have any suitable number of stimulation channels including, but not limited to, 4, 6, 8, 12, 16, 32, or more stimulation channels. The implantable pulse generator can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programed via wireless communications (e.g., Bluetooth) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated herein by reference.

Electrodes of the lead(s) (or electrodes of a sensor or other device) can be used to sense local electrical characteristics of the environment around the lead(s) and electrodes during and between electrical pulses or waveforms (which can be, for example, therapeutic stimulation pulses or waveforms, sub-perception pulses or waveforms, sensing pulses or waveforms, or other electrical pulses or waveforms). Examples of such sensing can include the measurement, recording, or observation of an electrophysiological signal, such as an evoked potential (EP), evoked compound action potential (ECAP), evoked resonant neural activity (ERNA), local field potential (LFP), ESG (electrospinogram), EEG (electroencephalogram), ECG (electrocardiogram), ECoG (electrocorticogram), or EMG (electromyogram) signal or the like or any combination thereof.

Figure 2A:
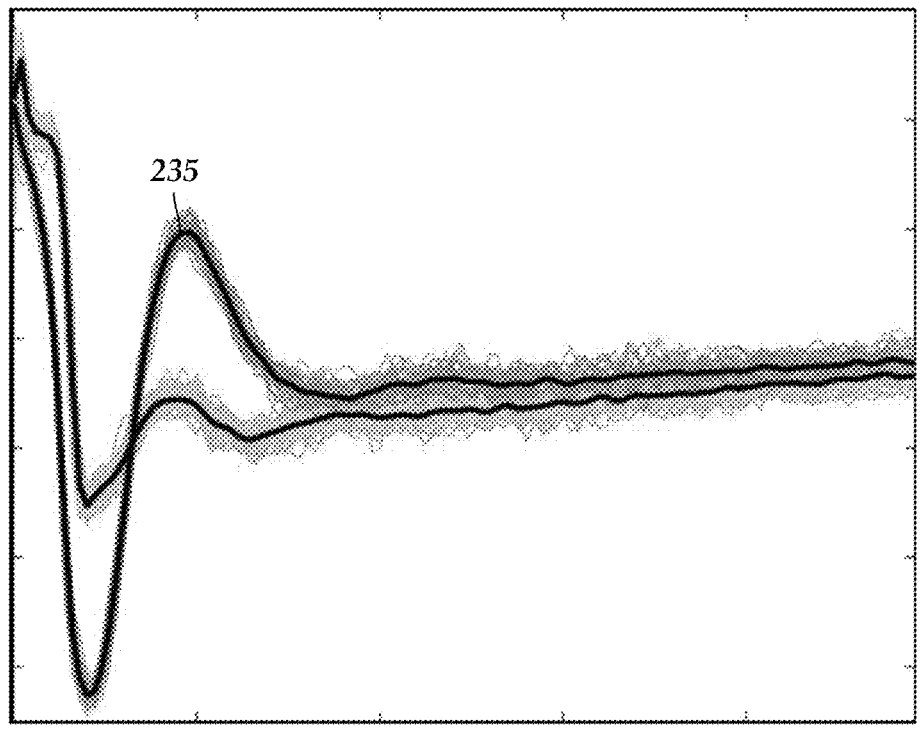
FIG. 2A is a schematic illustration of one embodiment of a neural response or neural signal.
Figure 2B:
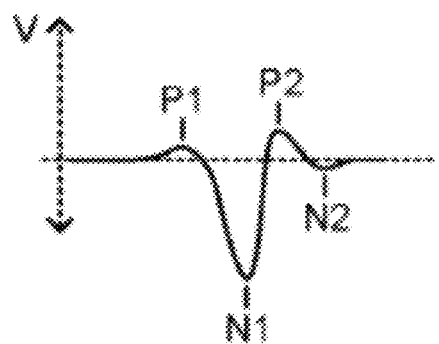
FIG. 2B is a schematic illustration of another embodiment of a neural response or neural signal.

Neural response signals or other neural signals, including, for example, an evoked potential (EP); evoked compound action potential (ECAP); evoked resonant neural activity (ERNA); local field potential (LFP); oscillations within the EEG, ECoG, LFP, or other neural signal; or the like or any combination thereof, can reflect the summed activity of different neural elements. For example, evoked potentials can capture those neurons directly activated by electrical stimulation. Evoked potentials may also reflect the propagation of neural activity across the neural network and may reflect both local and network level activation. FIG. 2A illustrates one example of a neural response 235 or neural signal. When a neural fiber is recruited by electrical stimulation, the neural fiber, in response, will issue an action potential—that is, the neural fiber will "fire." Should recruitment from electrical stimulation result in the neural fiber's resting state the neural fiber will depolarize, repolarize, and hyperpolarize before coming to rest again. If electrical stimulation continues, the neural fiber will fire again at some later time. FIG. 2B illustrates one example of an evoked compound action potential (ECAP) which can be a cumulative response of neural fibers recruited and firing within a volume.

Although features of the evoked potentials or other neural response signals can provide information about the neural environment, such features typically do not reveal the type of neural fibers that are activated. As described herein, in at least some embodiments, signal decomposition can be used to, for example, determine or estimate the underlying neural populations activated by stimulation. Use of signal decomposition may assist in improving stimulation targeting procedures.

Figure 3:
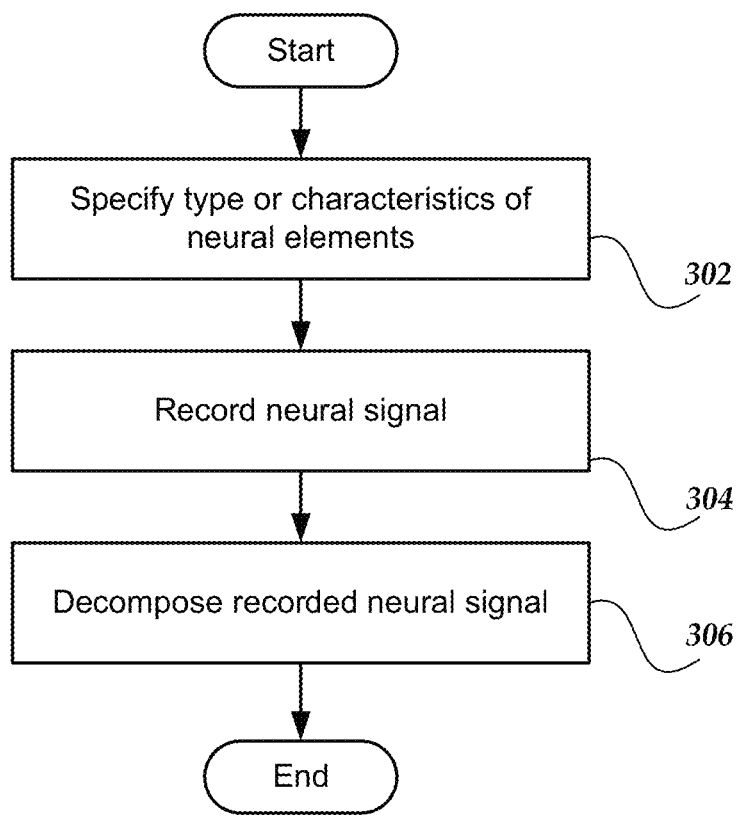
FIG. 3 is a flowchart of one embodiment of a method for estimating neural activation arising from stimulation by a stimulation system.

FIG. 3 illustrates one embodiment of a method for estimating neural activation arising from stimulation by a stimulation system. Such estimations may allow for estimation of which neural elements are activated or the amount of activation within a neural element population. In step 302, a user or a system specifies the types or characteristics of neural elements (for example, neural fibers, neural cells, axons, neural terminals, or other neural structures) that may be stimulated. For example, for deep brain stimulation, the specified neural elements may include anatomical structures such as the subthalamic nucleus (STN), globus pallidus interna (GPi), elements of the basal ganglia-thalamo-cortical loop (BGTC), or the like; specific neural tracts; or specific neural cells or cell groups; or the like or any combination thereof. For spinal cord stimulation, the specified neural elements may include, for example, A-beta or A-delta fibers or other specific neural cells or cell groups or neural structures or the like or any combination thereof. As another example, the different neural elements may be defined by one or more characteristics, such as, for example, the diameter, trajectory, orientation, or the like (or any combination thereof) of the neural fibers or neural cells. In at least some embodiments, the user or system designates the number of distinct neural signals that are expected in a neural response signal.

In at least some embodiments, the user can select some or all of the individual neural elements from a menu or a visual display. In at least some embodiments, the user can indirectly specify some or all of the neural elements by selecting anatomical regions, such as regions in the brain. The system can then supply one or more specific neural elements based on the user selection of the anatomical region. In at least some embodiments, knowledge about cells, axons, terminals, or other neural structures around the lead can be used to automatically specify some or all of the neural elements.

FIG. 6 illustrates one embodiment of a user interface 660 for selection of anatomical regions 662 or neural elements. In the illustrated embodiment, the STN anatomical region 662' has been selected. In the illustrated embodiment, the thalamus, GPi, globus pallidus externa (GPe), and internal capsule (IC) are also displayed as well as a representation of a lead 612. In at least some embodiments, the user interface 660 also presents a menu 664 for selection of different types of neural signals to allow the user to select the associated neural signal based on the selected anatomical region or neural element (e.g., the STN. In the illustrated embodiment, the menu 664 includes an Evoked Potential (EP), ERNA, LFP Template 1, and LFP Template 2. Other selections may be presented on the menu 664 depending on the selected anatomical region or neural element and on available templates or signals for the anatomical region or neural element. In at least some embodiments, the user or system can select one or more of these neural signals for the neural element. In at least some embodiments, the anatomical regions may be patient-specific based, for example, on patient images. In at least some embodiments, the anatomical regions may be based on an anatomical atlas or generalized model of the brain. In at least some embodiments, the anatomical regions can be a combination of patient-specific anatomical regions and anatomical regions based on an anatomical atlas or generalized model of the brain.

In step 304, a neural response signal is then recorded or otherwise obtained or measured. In step 306, the recorded neural response signal is decomposed into constituent neural signals for the individual neural elements to identify or determine the neural populations activated by stimulation. Examples of methods for decomposing the recorded neural response signal are described below.

In at least some embodiments, the decomposition of the recorded neural response signal includes assumptions that each of the types of neural elements produce a distinctive signal and that these signals from the neural elements can arrive at different periods in time depending, for example, on the distance from the stimulation source, the threshold amount of stimulation needed to produce a response, distance from the recording arrangement or the like or any combination thereof. As an example, in at least some embodiments, each type of neural element can contribute distinctive frequency components at specific timepoints in the signal to generate a composite neural response signal.

Figure 4:
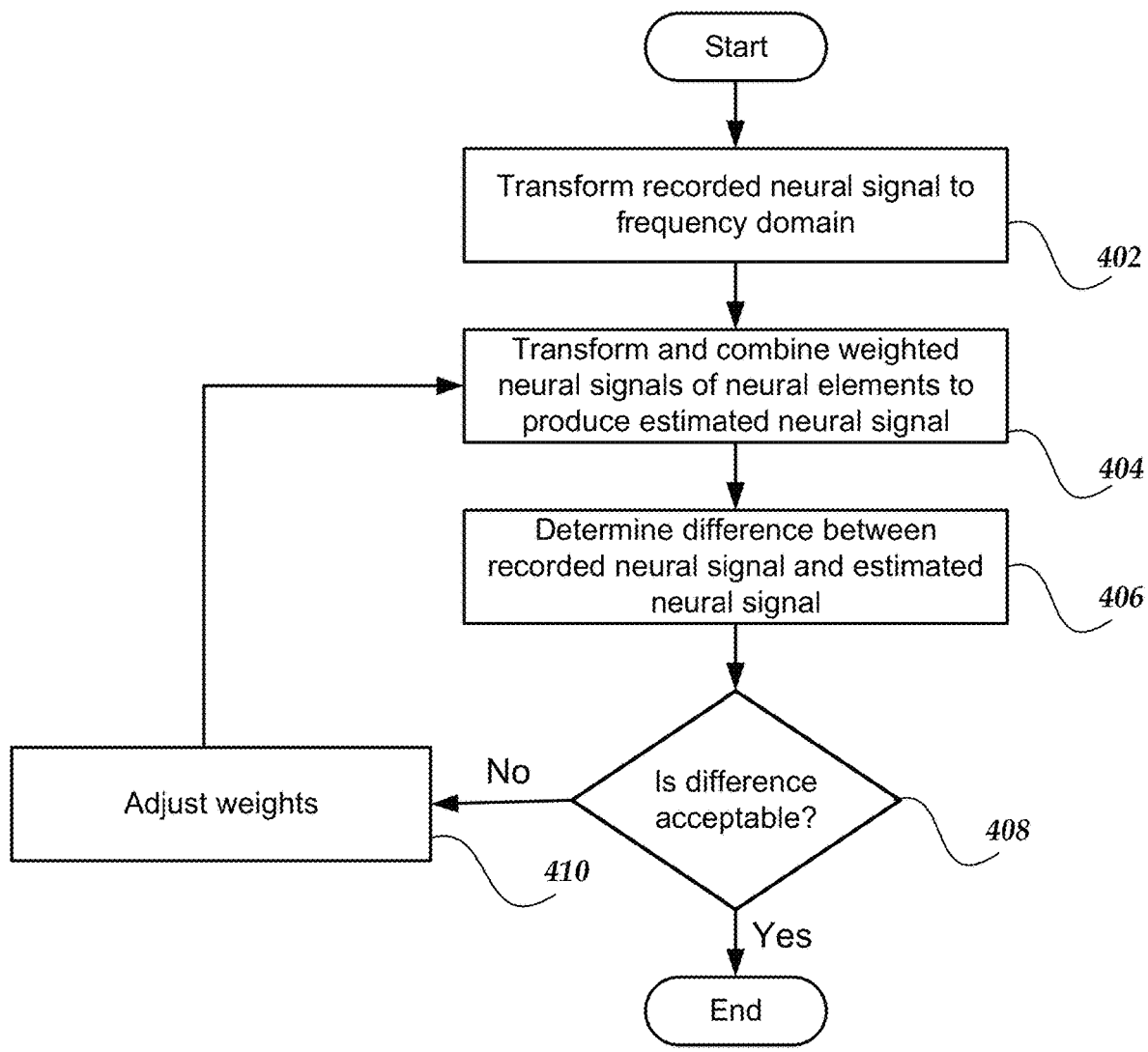
FIG. 4 is a flowchart of one embodiment of a method for decomposing the recorded neural response signal in the frequency domain.

FIG. 4 illustrates one embodiment of a method for decomposing the recorded neural response signal in the frequency domain. In step 402, the recorded neural response signal is transformed from the time domain to the frequency domain using any suitable technique, such as, for example, any suitable Fourier transform technique (e.g., a short-time Fourier transform (STFT)), or the like or any combination thereof.

In step 404, one or more neural signals (e.g., template signals) for each of the specified types of neural elements are selected, obtained, or otherwise provided. In at least some embodiments, the neural signals for each neural element are signals that have been previously recorded or extracted for those neural elements or are estimated signals generated from simulations, calculations, or models or any combination thereof.

FIG. 7A illustrates one embodiment of a user interface for selecting which neural signals to use for the neural elements. In section 772, the individual neural signals can be selected. In at least some embodiments, the selection can be made from a menu or using up/down arrows 774. In the illustrated embodiment, the STN ERNA, STN EP, and IC EP signals are selected. In optional section 776, the source for a neural signal can be selected by a user including a pre-loaded (e.g., default or stored) signal, an acquired signal, or a custom (e.g., user-provided) signal. In at least some embodiments, if the custom signal is selected, a prompt appears asking the user to upload the custom signal in an appropriate format (e.g., a .dat format). In at least some embodiments, the user or system may select a portion of the neural signal to use in the composite signal. FIG. 7B illustrates examples of neural signals 775 that can be used as templates for the selected neural signals.

In at least some embodiments, the system may send a warning to a user if two or more of the selected neural signals are of different time lengths or are too similar (which may indicate, for example, that the same neural signal has been selected twice).

Returning to step 404 of FIG. 4, the selected neural signals are transformed (if not already transformed) into the frequency domain. These neural signals can be combined into a composite neural signal using individual weights for each of the neural elements to reflect the strength of the signal expected for the population of the specific neural elements. The combined neural signals form an estimated neural signal. The weights can be relative weights (for example, relative to a weight of 1 for one of the neural signals), absolute weights, or weights that sum to 100 (e.g., 100 percent) or 1 or any other suitable number. The combination, and associated weighting, can utilize linear or non-linear models or combinations.

In at least some embodiments, the distinct frequencies for the neural signal(s) from each neural element may be used to create an a priori estimate of the initial weight for each neural element or neural signal. In at least some embodiments, the user or the system may provide an initial estimate of the weight for each of the neural elements. As an example, in the user interface of FIG. 7A, in section 778 of the user interface the user can select the initial relative weights for each of the signals. In at least some embodiments, the initial estimate of the weights can be based on, for example, literature sources, clinician experience, any other suitable source, or the like or any combination thereof. In at least some embodiments, the system may perform an initial weight estimate using any suitable technique including, but not limited to, least squares fitting, generalized linear model (GLM) regression, other regression techniques, QR factorization, machine learning techniques (for example, fuzzy logic, neural networks, k-nearest neighbor (KNN) techniques, density-based unsupervised clustering, Gaussian mixture models, support vector machine-based supervised methods, hierarchical clustering, or the like), coordinate descent, gradient descent, or the like or any combination thereof.

In at least some embodiments, the system may alert a user if neural signals from two or more of the neural elements have known covariance that exceeds or meets a threshold amount. In other embodiments, the system may alter or select weights based on the known covariance.

FIG. 7D illustrates another embodiment of a user interface 779 that may be provided in addition to, or as an alternative to, section 778 of FIG. 7A. The user interface 779 of FIG. 7D allow the user to select an initial weight for the neural signals that is equal, preset/unequal, or preset/custom. The "preset, unequal" selection in FIG. 7D may be useful when it is known that activation of a certain neural element will intrinsically produce a larger signal than activation of another neural element (for example, due to more of the first neural element than the second or a larger intrinsic response.) If the "preset, custom" selection in FIG. 7D is made, the user can be prompted to enter weights for one or more of the neural signals. In at least some embodiments, if a weight is not entered for the neural signal, a default value (for example, 0, 1, or 100) is used.

In at least some embodiments, the system can filter the neural response signal or the neural signal(s) for each neural element or any combination thereof. In at least some embodiments, the same filters is applied to both the neural response signal and the individual neural signals. The filtering can be based on, for example, lead impedance, device measurement settings (for example, sampling rate or sample averaging), or the like or any combination thereof. In at least some embodiments, the user can set the filter(s). The filters can include, for example, hardware/analog filters, amplifier gain level, artifact blanking settings, least mean square (LMS) artifact cancellation filters, adaptive filters, or digital FIR filters, or the like or any combination thereof.

Figure 8:
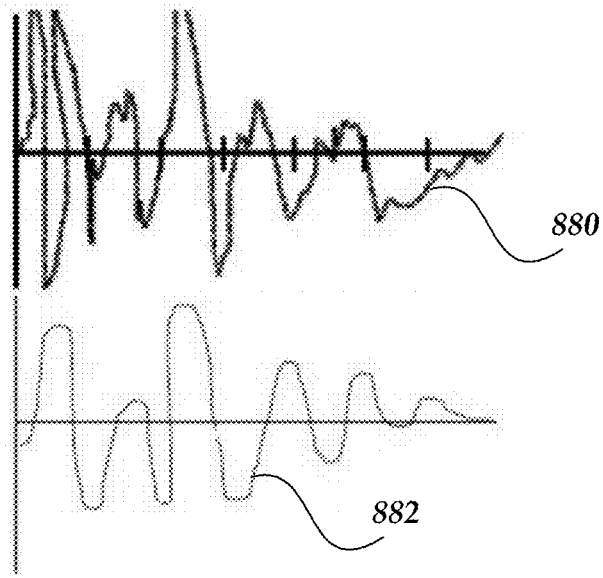
FIG. 8 is a schematic representation of neural signal before and after filtering.
Figure 9:
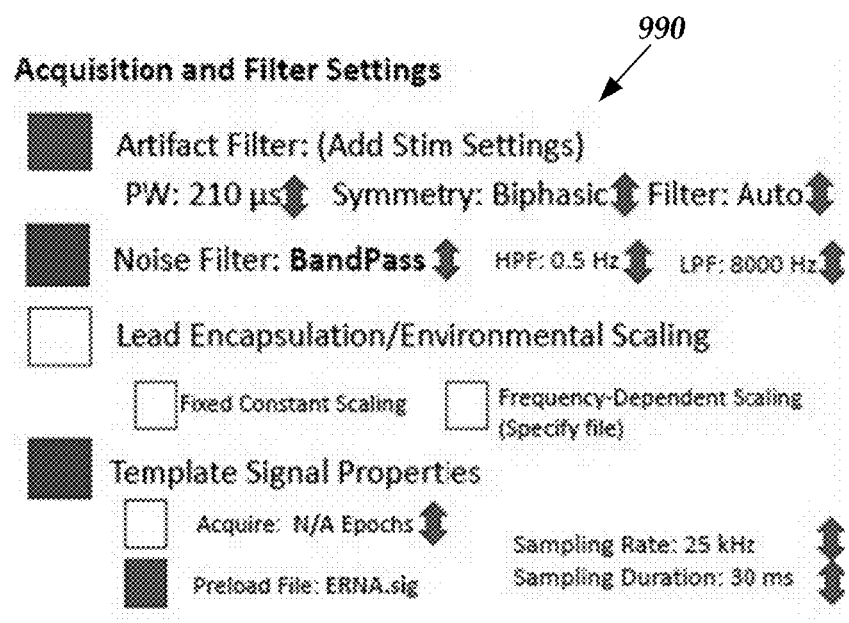
FIG. 9 is a schematic representation of one embodiment of a user interface for selecting filters or other signal processing.

FIGS. 8 and 9 illustrate filtering or other signal processing of the recorded response signal or the neural signal(s) for the individual neural elements. In FIG. 8, the acquired response or selected neural signal 880 is illustrated along with a filtered signal 882 obtained by filtering the signal 880.

FIG. 9 illustrates one embodiment of a user interface 990 for selecting filters or other signal processing. Examples of filters and other signal processing include, but are not limited to, an artifact filter, a noise filter, lead encapsulation/environmental scaling, and template signal properties. The artifact filter can be used, for example, to remove any artifact arising from the stimulation signal that generates the neural response. The artifact filter may include user input such as the pulse width, amplitude, type of stimulation (e.g., biphasic, monophasic, or the like), and the type of filter. The noise filter can be a low pass, high pass, or bandpass filter and may include a user- or system-selected high pass frequency or a user- or system-selected low pass frequency, as appropriate for the type of filter. The lead encapsulation/environmental scaling may account for tissue differences near the lead, such as an encapsulation layer adjacent to the lead, and may provide fixed or frequency-dependent scaling.

The recorded neural response signal may also be filtered based on the properties of the other neural signals such as, for example, sampling rate, sampling duration, or the like or any combination thereof. It will be understood that the filtering or other signal processing can be applied to the recorded neural response signal or the other neural signals or any combination thereof. In at least some embodiments, the same filtering or other signal processing may be applied to both the recorded neural response signal and the other neural signals.

In at least some embodiments, the user may input the lead implant site or estimated distance(s) between the lead and the neural elements. In at least some embodiments, the system may estimate the distance between the lead and the neural elements based on the lead implant site. The system may use the distance information to modify the expected amplitude or other features of any of the neural signal(s) from the individual neural elements.

Figure 10:
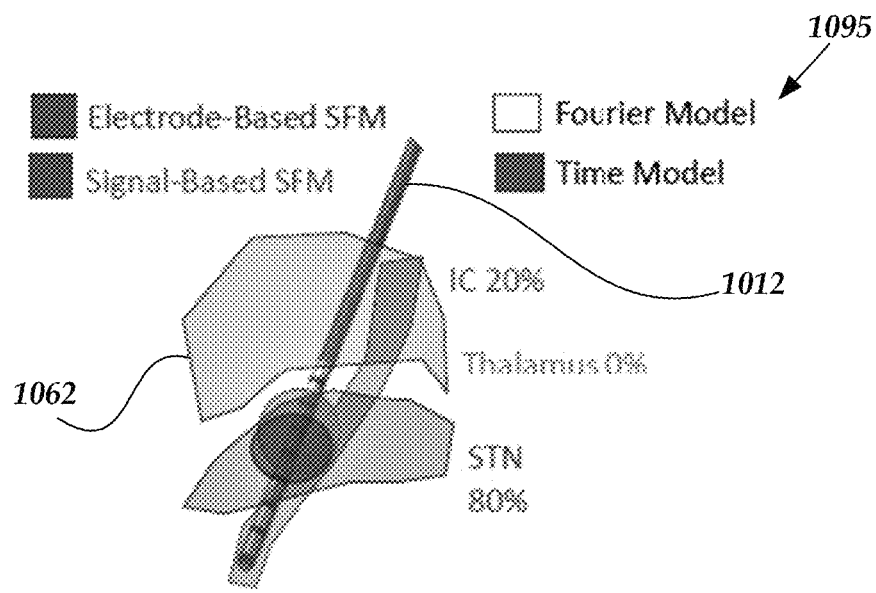
FIG. 10 is a schematic representation of one embodiment of a user interface for selecting filters or other signal processing.

FIG. 10 illustrates an example of a user interface 1095 with illustrates a lead 1012 and anatomical structures 1062. The user interface also includes a stimulation field model (SFM) that is calculated based on stimulation parameters (for example, electrode selection, amplitude, pulse width, pulse duration, or the like or any combination thereof) and illustrates the estimated volume of activation (VOA) of tissue that will be activated by the stimulation. Examples of the SFM or VOA, as well as methods and systems for determining the SFM or VOA, can be found at U.S. Pat. Nos. 8,326,433; 8,379,952; 8,649,845; 8,675,945; 8,831,731; 8,849,632; 8,855,773; 8,913,804; 8,918,183; 8,958,615; 9,026,317; 9,050,470; 9,072,905; 9,081,488; 9,084,896; 9,135,400; 9,227,074; 9,235,685; 9,254,387; 9,272,153; 9,302,110; 9,308,372; 9,310,985; 9,364,665; 9,526,902; 9,586,053; 9,792,412; 9,821,167; 9,925,382; and 9,959,940; U.S. Patent Application Publications Nos. 2009/0287272; 2009/0287273; 2012/0314924; 2013/0116744; 2014/0122379; 2015/0066111; 2016/0375248; 2016/0375258; and 2017/0304633; U.S. patent application Ser. Nos. 15/706,004; 15/864,876; and Ser. No. 15/937,264; and U.S. Provisional Patent Application Ser. Nos. 62/030,655 and 62/532,869, all of which are incorporated herein by reference in their entireties.

Figure 11:
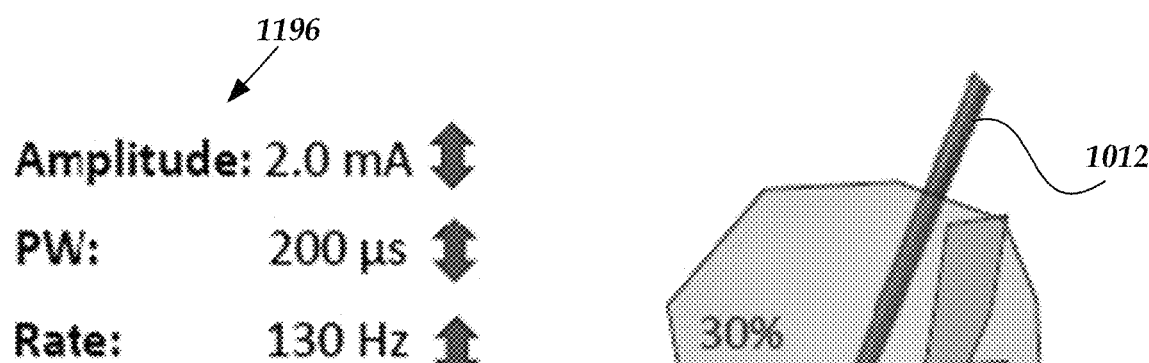
FIG. 11 is a schematic representation of one embodiment of a user interface for inputting stimulation parameters.

In at least some embodiments, the user or system may provide or input stimulation settings such as electrode selection, stimulation rate, stimulation duration, pulse width, amplitude, or the like or any combination thereof. The system may use the stimulation settings to adjust the neural signals that arise in response to the stimulation, for example, if those neural signals are known to be sensitive or dependent on one or more of those stimulation settings. FIG. 11 illustrates one embodiment of a user interface 1196 for inputting stimulation parameters such as amplitude, pulse width (PW), or pulse rate.

In step 406, the difference between the recorded neural response signal and the estimated neural signal is determined. The difference can be determined using any suitable technique such as, for example, mean squared error, a binned mean squared error, mean rectified error, statistical analyze of features of the signal (for example, comparing a mean and standard deviation of a signal feature from template signals versus the mean and standard deviation for the feature of the recorded signal, or the like or any combination thereof. In at least some embodiments, the feasibility, fitness, or robustness of the determined weights can be compared versus a predictor model that can be based on expected physiological models or the like. If the determined weights are not within a threshold difference from the predictor model, the system may alert the user.

Figure 12:
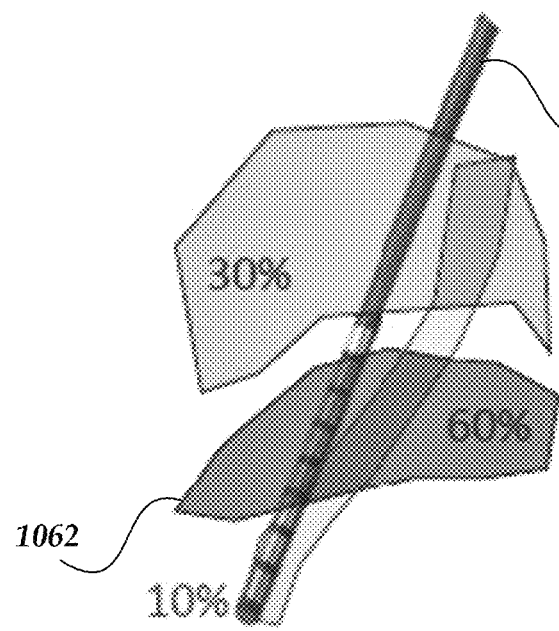
FIG. 12 is a schematic representation of one embodiment of determined weights for a stimulation.

In step 408, the system determines whether the difference is acceptable or not. For example, the system may determine whether the difference meets or exceeds a threshold amount and, if so, whether the difference is unacceptable. If the difference is acceptable, the process ends. FIG. 12 illustrates one example of determined weights for a stimulation: 60% STN, 30% Thalamus, and 10% IC.

If the difference is not acceptable, the weights are adjusted in step 410 and the process returns to step 404. In at least some embodiments, the weight adjustment may be requested from the user. In at least some embodiments, the system may perform the weight adjustment using any suitable technique including, but not limited to, least squares fitting, generalize linear model (GLM) regression, other regression techniques, QR factorization, machine learning techniques (for example, fuzzy logic, neural networks, k-nearest neighbor (KNN) techniques, density-based unsupervised clustering, Gaussian mixture models, support vector machine-based supervised methods, hierarchical clustering, or the like or any combination thereof), coordinate descent, gradient descent, or the like or any combination thereof. The process can continue until acceptable weights are found or the system or user halts the process.

Figure 5:
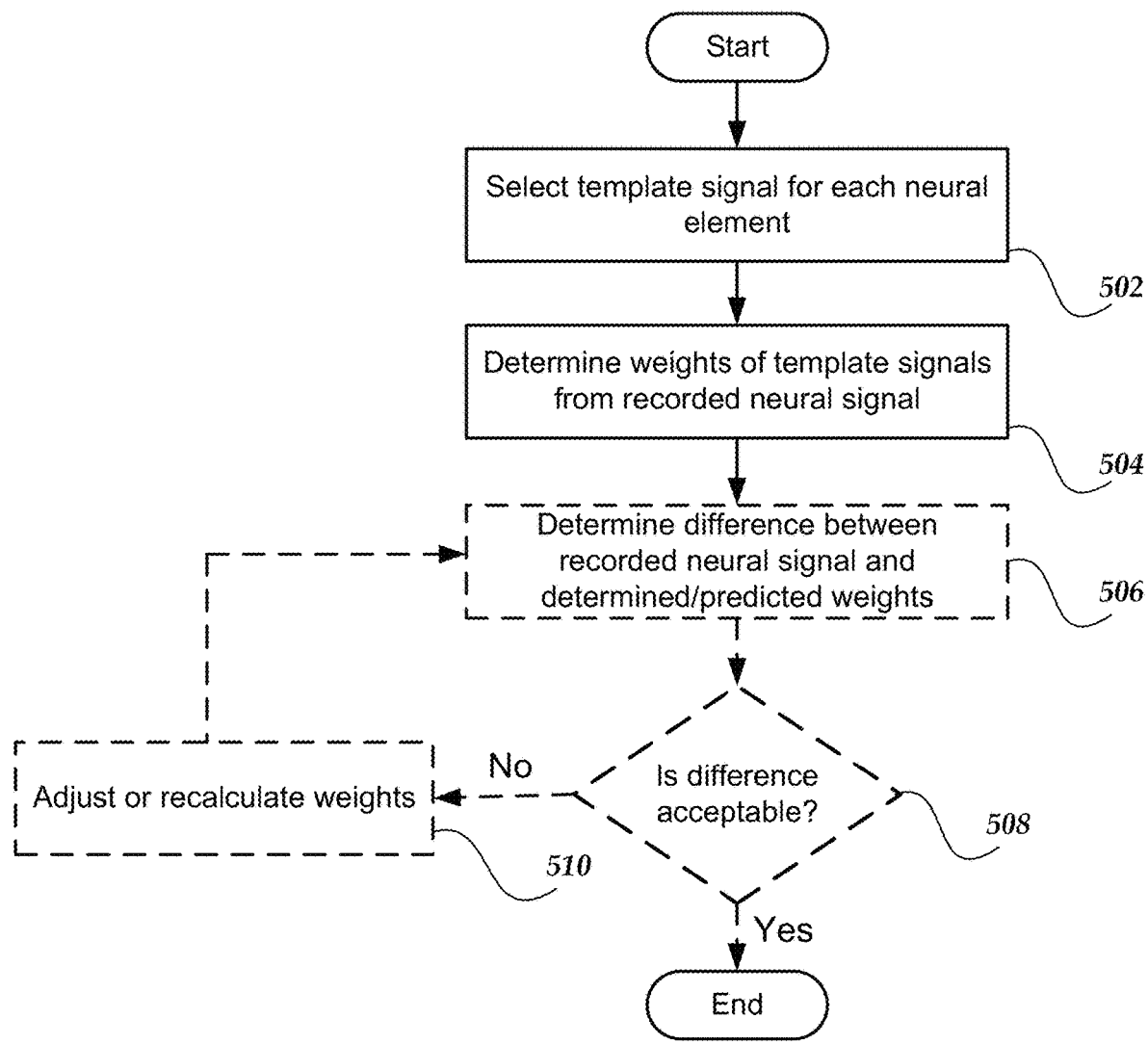
FIG. 5 is a flowchart of one embodiment of a method for decomposing the recorded neural response signal in the time domain.

FIG. 5 illustrates one embodiment of a method for decomposing the recorded signal in the time domain. In step 502, template signals for each of the specified types of neural elements are selected. FIG. 7B illustrates examples of neural signals 775 that can be used as templates for the selected neural signals. In at least some embodiments, the template signals for each neural element are signals that have been previously recorded or extracted for those neural elements or are estimated signals generated from simulations, calculations, or models or any combination thereof. The same considerations and options described above with respect to the method illustrated in FIG. 4 are applicable to the method illustrated in FIG. 5, including all of the considerations and options illustrated in FIG. 7A to FIG. 12.

In step 504, weights for the template signals are determined from the recorded neural signal. The system performs a weight determination using any suitable technique including, but not limited to, least squares fitting, generalized linear model (GLM) regression, other regression techniques, QR factorization, machine learning techniques (for example, fuzzy logic, neural networks, k-nearest neighbor (KNN) techniques, density-based unsupervised clustering, Gaussian mixture models, support vector machine-based supervised methods, hierarchical clustering, or the like), coordinate descent, gradient descent, or the like or any combination thereof. FIG. 7C illustrates a composite signal 777 of the three template signals of FIG. 7B combined using weights (for example, 10% of $S_1$, 30% of $S_2$, and 60% of $S_3$), as described in more detail below.

In at least some embodiments, the process ends with step 504. In other embodiments, the resulting composite signal may be compared with the neural response signal or a predicted or estimated neural signal. In at least some other embodiments, the user or the system may provide a predicted estimate of the weight for each of the neural elements using, for example, literature sources, clinician experience, any other suitable source, or the like or any combination thereof. In at least some embodiments, the feasibility, fitness, or robustness of the determined weights can be compared versus a predictor model that can be based on expected physiological models or the like.

In optional step 506, the difference between the recorded neural response signal and composite signal generated using the estimated or predicted weights (or the predicted or estimated neural signal) is determined. The difference can be determined using any suitable technique such as, for example, mean squared error, a binned mean squared error, mean rectified error, statistical analyze of features of the signal (for example, comparing a mean and standard deviation of a signal feature from template signals versus the mean and standard deviation for the feature of the recorded signal, or the like or any combination thereof.

In optional step 508, the system determines whether the difference is acceptable or not. For example, the system may determine whether the difference meets or exceeds a threshold amount and, if so, the difference is unacceptable. For example, in at least some embodiments, if the determined weights are not within a threshold difference from the predictor model, the system may alert the user. If the difference is acceptable, the process ends.

If the difference is not acceptable, the weights are adjusted or recalculated in optional step 510 and the process returns to step 506. In at least some embodiments, the weight adjustment may be requested from the user. In at least some embodiments, the system may perform the weight adjustment using any suitable technique including, but not limited to, least squares fitting, generalize linear model (GLM) regression, other regression techniques, QR factorization, machine learning techniques (for example, fuzzy logic, neural networks, k-nearest neighbor (KNN) techniques, density-based unsupervised clustering, Gaussian mixture models, support vector machine-based supervised methods, hierarchical clustering, or the like), coordinate descent, gradient descent, or the like or any combination thereof. The process can continue until acceptable weights are found or the system or user halts the process.

It will be understood that the methods illustrated in FIGS. 4 and 5 can be modified to apply to either time domain or frequency domain methods or any combination thereof. It will be understood that each block of the flowchart illustration, and combinations of blocks in the flowchart illustration and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computing device. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, cloud-based storage, or any other medium which can be used to store the desired information and which can be accessed by a computing device.

Figure 13:
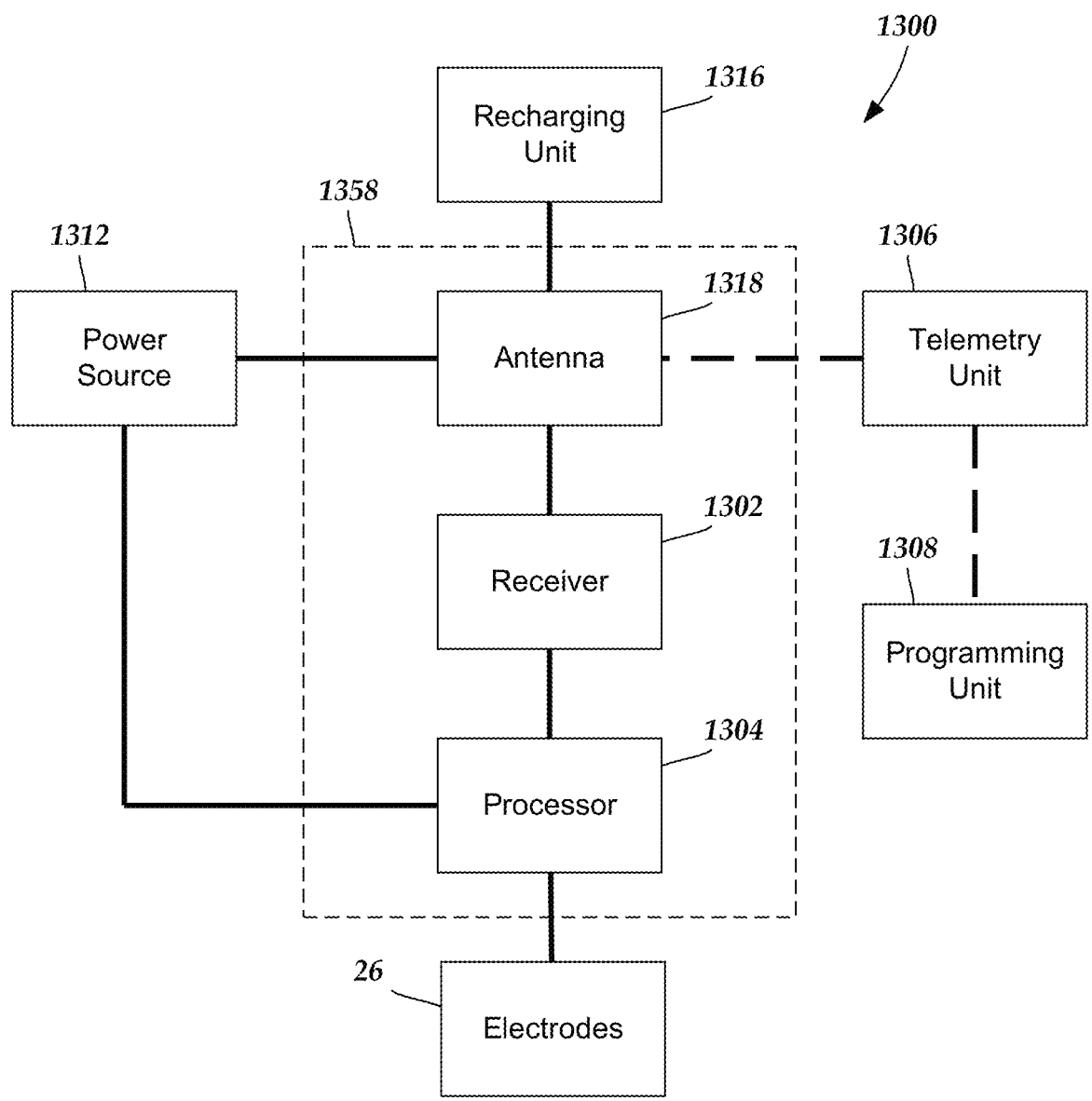
FIG. 13 is a schematic overview of one embodiment of components of a stimulation system, including an electronic subassembly disposed within a control module.

FIG. 13 is a schematic overview of one embodiment of components of an electrical stimulation system 1300 including an electronic subassembly 1358 disposed within a control module. The electronic subassembly 1358 may include one or more components of the IPG. It will be understood that the electrical stimulation system can include more, fewer, or different components and can have a variety of different configurations including those configurations disclosed in the stimulator references cited herein.

Some of the components (for example, a power source 1312, an antenna 1318, a receiver 1302, and a processor 1304) of the electrical stimulation system can be positioned on one or more circuit boards or similar carriers within a sealed housing of an implantable pulse generator (see e.g., 14 in FIG. 1), if desired. Any power source 1312 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1318 or a secondary antenna. In at least some embodiments, the antenna 1318 (or the secondary antenna) is implemented using the auxiliary electrically-conductive conductor. The external power source can be in a device that is mounted on the skin of the user or in a unit that is provided near the user on a permanent or periodic basis.

If the power source 1312 is a rechargeable battery, the battery may be recharged using the optional antenna 1318, if desired. Power can be provided to the battery for recharging by inductively coupling the battery through the antenna to a recharging unit 1316 external to the user. Examples of such arrangements can be found in the references identified above. The electronic subassembly 1358 and, optionally, the power source 1312 can be disposed within a control module (e.g., the IPG 14 or the ETS 20 of FIG. 1).

In one embodiment, electrical stimulation signals are emitted by the electrodes 26 to stimulate nerve fibers, muscle fibers, or other body tissues near the electrical stimulation system. The processor 1304 is generally included to control the timing and electrical characteristics of the electrical stimulation system. For example, the processor 1304 can, if desired, control one or more of the timing, frequency, strength, duration, and waveform of the pulses. In addition, the processor 1304 can select which electrodes can be used to provide stimulation, if desired. In some embodiments, the processor 1304 selects which electrode(s) are cathodes and which electrode(s) are anodes. In some embodiments, the processor 1304 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1308 that, for example, allows modification of pulse characteristics. In the illustrated embodiment, the processor 1304 is coupled to a receiver 1302 which, in turn, is coupled to the optional antenna 1318. This allows the processor 1304 to receive instructions from an external source to, for example, direct the pulse characteristics and the selection of electrodes, if desired.

In one embodiment, the antenna 1318 is capable of receiving signals (e.g., RF signals) from an external telemetry unit 1306 which is programmed by the programming unit 1308. The programming unit 1308 can be external to, or part of, the telemetry unit 1306. The telemetry unit 1306 can be a device that is worn on the skin of the user or can be carried by the user and can have a form similar to a pager, cellular phone, or remote control, if desired. As another alternative, the telemetry unit 1306 may not be worn or carried by the user but may only be available at a home station or at a clinician's office. The programming unit 1308 can be any unit that can provide information to the telemetry unit 1306 for transmission to the electrical stimulation system 1300. The programming unit 1308 can be part of the telemetry unit 1306 or can provide signals or information to the telemetry unit 1306 via a wireless or wired connection. One example of a suitable programming unit is a computer operated by the user or clinician to send signals to the telemetry unit 1306.

The signals sent to the processor 1304 via the antenna 1318 and the receiver 1302 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1300 to cease operation, to start operation, to start charging the battery, or to stop charging the battery. In other embodiments, the stimulation system does not include the antenna 1318 or receiver 1302 and the processor 1304 operates as programmed.

Optionally, the electrical stimulation system 1300 may include a transmitter (not shown) coupled to the processor 1304 and the antenna 1318 for transmitting signals back to the telemetry unit 1306 or another unit capable of receiving the signals. For example, the electrical stimulation system 1300 may transmit signals indicating whether the electrical stimulation system 1300 is operating properly or not or indicating when the battery needs to be charged or the level of charge remaining in the battery. The processor 1304 may also be capable of transmitting information about the pulse characteristics so that a user or clinician can determine or verify the characteristics.

Figure 14:
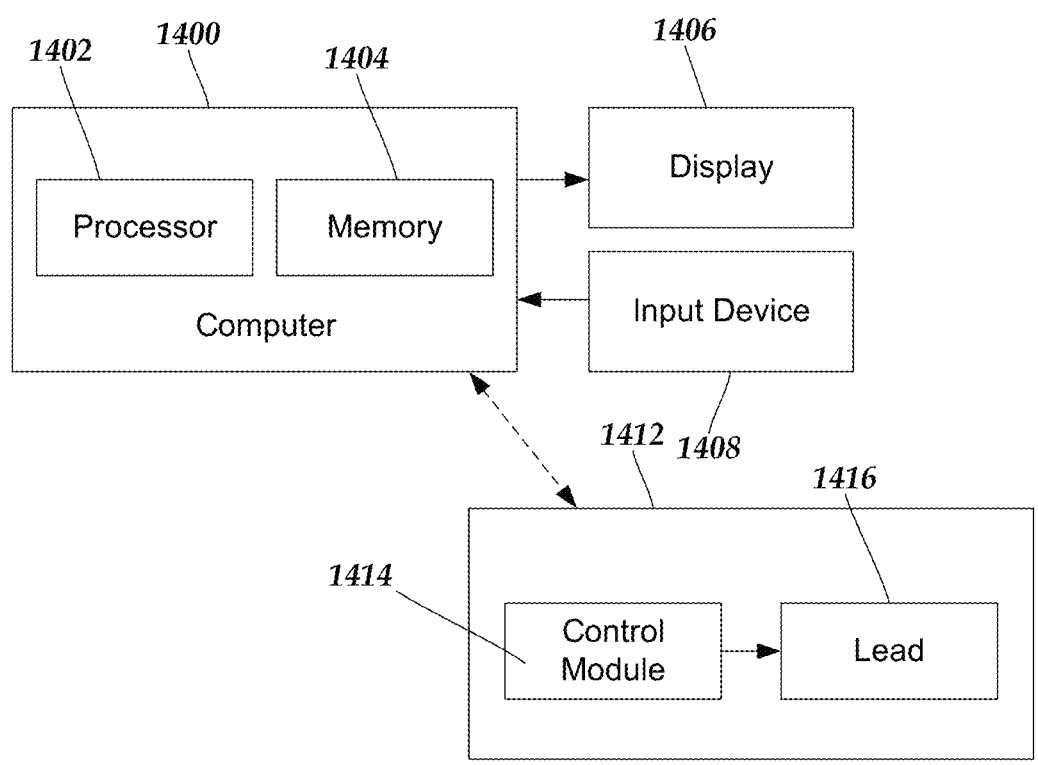
FIG. 14 is a schematic block diagram of a system for practicing the methods described herein.

FIG. 14 illustrates one embodiment of a system for practicing any of the methods described herein. The system can include a computer 1400 or any other similar device that includes at least one processor 1402 and a memory 1404, a display 1406, an input device 1408 and, optionally, the electrical stimulation system 1412.

The computer 1400 can be a laptop computer, desktop computer, tablet, mobile device, smartphone, or other devices that can run applications or programs, or any other suitable device for processing information and for presenting a user interface. The computer can be, for example, the CP 18 or RC 16 of FIG. 1 or the programming unit 1308 of FIG. 13. The computer 1400 can be local to the user or can include components that are non-local to the user including one or both of the processor 1402 or memory 1404 (or portions thereof). For example, in some embodiments, the user may operate a terminal that is connected to a non-local computer. In other embodiments, the memory can be non-local to the user. As another example, the computer 1400 may utilize or communicate with a processor in the control module 1414 (such as the IPG 14 or ETS 20 of FIG. 1).

The computer 1400 can utilize any suitable processor 1402 including one or more hardware processors that may be local to the user or non-local to the user or other components of the computer. The processor 1402 is configured to execute instructions provided to the processor, as described below.

Any suitable memory 1404 can be used for the processor 1402. The memory 1404 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computer.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 1406 can be any suitable display device, such as a monitor, screen, display, or the like, and can include a printer. The input device 1408 can be, for example, a keyboard, mouse, touch screen, track ball, joystick, voice recognition system, or any combination thereof, or the like and can be used by the user to interact with a user interface or clinical effects map.

The electrical stimulation system 1412 can include, for example, a control module 1414 (for example, the IPG 14 or ETS 20 of FIG. 1) and a lead 1416 (for example, the lead 12 illustrated in FIG. 1.) The electrical stimulation system 1412 may communicate with the computer 1400 through a wired or wireless connection or, alternatively or additionally, a user can provide information between the electrical stimulation system 1412 and the computer 1400 using a computer-readable medium or by some other mechanism. In some embodiments, the computer 1400 may include part of the electrical stimulation system. In at least some embodiments, the computer 1400 can program the control module 1414 for delivery of stimulation pulses, charge recovery pulse, charge recovery phases, or the like or any combination thereof.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A method for estimating neural activation arising from deep brain stimulation by a stimulation system, the method comprising:
   identifying a plurality of different anatomical structures of a brain stimulated by the deep brain stimulation;
   for each of the different anatomical structures of the brain, providing at least one template signal for the anatomical structure of the brain;
   obtaining a neural response signal resulting from the deep brain stimulation by the stimulation system;
   decomposing the neural response signal in a time domain into a plurality of decomposed signals using the template signals to estimate neural activation of each of the different anatomical structures of the brain, wherein decomposing the neural response signal comprises decomposing the neural response signal using the template signals, wherein decomposing the neural response signal comprises determining weights for each of the template signals as portions of the neural response signal;
   combining the template signals using the weights to generate a composite neural signal; and
   using the estimated neural activations of each of the different anatomical structures of the brain to adjust stimulation settings of the stimulation system.

2. The method of claim 1, further comprising determining a difference between the neural response signal and the composite neural signal.

3. The method of claim 2, further comprising determining when the difference exceeds a predetermined threshold difference and, when so, adjusting the weights.

4. The method of claim 1, further comprising filtering the neural response signal.

5. The method of claim 1, wherein the plurality of different anatomical structures of the brain comprises at least one of the thalamus, subthalamic nucleus, globus pallidus interna, globus pallidus externa, or internal capsule.

6. The method of claim 1, further comprising displaying a representation of at least a portion of the brain and receiving selections by a user from the representation of the plurality of different anatomical structures of the brain for deep brain stimulation.

7. The method of claim 1, further comprising, for each of the different anatomical structures of the brain, receiving a selection of a type of signal to be used for the template signal.

8. A method for estimating neural activation arising from deep brain stimulation by a stimulation system, the method comprising:
   identifying a plurality of different anatomical structures of a brain stimulated by the deep brain stimulation;
   for each of the different anatomical structures of the brain, providing at least one template signal for the anatomical structure of the brain;
   determining initial weights for each of the template signals using one or more distinctive frequency components in the template signals;
   obtaining a neural response signal resulting from the deep brain stimulation by the stimulation system;
   transforming the neural response signal into a frequency domain;
   decomposing the neural response signal in the frequency domain into a plurality of decomposed signals using the template signals to estimate neural activation of each of the different anatomical structures of the brain, wherein decomposing the neural response signal comprises determining weights for each of the template signals as portions of the neural response signal; and
   using the estimated neural activations of each of the different anatomical structures of the brain to adjust stimulation settings of the stimulation system.

9. The method of claim 8, further comprising displaying a representation of at least a portion of the brain and receiving selections by a user from the representation of the plurality of different anatomical structures of the brain for deep brain stimulation.

10. The method of claim 8, further comprising, for each of the different anatomical structures of the brain, receiving a selection of a type of signal to be used for the template signal.

11. The method of claim 8, further comprising filtering the neural response signal.

12. The method of claim 8, wherein the plurality of different anatomical structures of the brain comprises at least one of the thalamus, subthalamic nucleus, globus pallidus interna, globus pallidus externa, or internal capsule.

13. The method of claim 8, further comprising combining the template signals using the weights to generate a composite neural signal.

14. A method for estimating neural activation arising from deep brain stimulation by a stimulation system, the method comprising:
   identifying a plurality of different anatomical structures of a brain stimulated by the deep brain stimulation;

for each of the different anatomical structures of the brain, providing at least one template signal for the anatomical structure of the brain;

obtaining a neural response signal resulting from the deep brain stimulation by the stimulation system;

transforming the neural response signal into the frequency domain;

decomposing the neural response signal in the frequency domain into a plurality of decomposed signals using the template signals to estimate neural activation of each of the different anatomical structures of the brain, wherein decomposing the neural response signal comprises determining weights for each of the template signals as portions of the neural response signal;

combining the template signals using the weights to generate a composite neural signal; and using the estimated neural activations of each of the different anatomical structures of the brain to adjust stimulation settings of the stimulation system.

15. The method of claim 14, further comprising determining a difference between the neural response signal and the composite neural signal.

16. The method of claim 15, further comprising determining when the difference exceeds a predetermined threshold difference and, when so, adjusting the weights.

17. The method of claim 14, further comprising displaying a representation of at least a portion of the brain and receiving selections by a user from the representation of the plurality of different anatomical structures of the brain for deep brain stimulation.

18. The method of claim 14, further comprising, for each of the different anatomical structures of the brain, receiving a selection of a type of signal to be used for the template signal.

19. The method of claim 14, further comprising filtering the neural response signal.

20. The method of claim 14, wherein the plurality of different anatomical structures of the brain comprises at least one of the thalamus, subthalamic nucleus, globus pallidus interna, globus pallidus externa, or internal capsule.

* * * * *